(12) United States Patent
Tian et al.

(10) Patent No.: US 10,184,917 B2
(45) Date of Patent: Jan. 22, 2019

(54) METHOD FOR AUTOMATICALLY IDENTIFYING RESONANCE

(71) Applicant: LINESTREAM TECHNOLOGIES, Cleveland, OH (US)

(72) Inventors: Gang Tian, Westlake, OH (US); Chris Knaack, Bay Village, OH (US)

(73) Assignee: LINESTREAM TECHNOLOGIES, Cleveland, OH (US)

( * ) Notice: Subject to any disclaimer, the term of this patent is extended or adjusted under 35 U.S.C. 154(b) by 219 days.

(21) Appl. No.: 15/259,286

(22) Filed: Sep. 8, 2016

(65) Prior Publication Data
US 2018/0067086 A1 Mar. 8, 2018

(51) Int. Cl.
*G01N 29/12* (2006.01)
*G01N 29/22* (2006.01)
(Continued)

(52) U.S. Cl.
CPC .............. *G01N 29/42* (2013.01); *G01N 29/12* (2013.01); *G01N 29/225* (2013.01); *G01N 29/449* (2013.01); *G01N 29/4454* (2013.01); *G01N 29/4463* (2013.01); *G01N 29/4472* (2013.01); *H02P 23/14* (2013.01); *G01N 2291/014* (2013.01); *G01N 2291/015* (2013.01)

(58) Field of Classification Search
CPC .. G01N 29/42; G01N 29/4463; G01N 29/449; G01N 2291/014; H02P 23/14
USPC .......................................................... 73/579
See application file for complete search history.

(56) References Cited

U.S. PATENT DOCUMENTS

| 4,084,428 A | * | 4/1978 | Ahn | ...................... G01R 31/343 |
| | | | | 73/114.13 |
| 5,594,175 A | * | 1/1997 | Lyon | ...................... F16K 31/04 |
| | | | | 73/168 |

(Continued)

OTHER PUBLICATIONS

Ellis, et al. "Resonant Load Control Methods for Industrial Servo Drives", IEEE Industry Application Society, Annual Meeting, Rome, Italy, Oct. 8-12, 2000. Retrieved on Oct. 20, 2016, 8 pages.
(Continued)

*Primary Examiner* — J M Saint Surin
(74) *Attorney, Agent, or Firm* — Amin, Turocy & Watson LLP

(57) ABSTRACT

A resonance estimation system implements resonance detection methods that can obtain accurate estimates of a motion system's resonance and amplitude without the need for a high-resolution encoder or high-frequency sampling. The system solves for resonance information by removing the slow motion dynamics and fast torque control dynamics from the measured speed transfer function in order to obtain resonance transfer function. Smoothing functions are applied to the obtained resonance frequency response data to remove spikes and obtain relatively smooth gain and phase curves for the resonance frequency response. The system then applies a searching algorithm to determine the locations of the phase peaks in the phase curve data, and uses these phase peak locations to locate the gain peaks in the gain curve data, which correspond to the resonance frequencies and amplitudes. This approach allows the gain peaks to be located even when analyzing non-ideal gain curves that are degraded by noise.

17 Claims, 19 Drawing Sheets

(51) Int. Cl.
*G01N 29/44* (2006.01)
*H02P 23/14* (2006.01)
*G01N 29/42* (2006.01)

(56) References Cited

U.S. PATENT DOCUMENTS

| | | |
|---|---|---|
| 6,979,967 B2 | 12/2005 | Ho |
| 7,023,168 B1 | 4/2006 | Patel et al. |
| 7,193,799 B2 | 3/2007 | Chung |
| 7,339,344 B2 | 3/2008 | Borisavljevic |
| 7,714,529 B2 | 5/2010 | Chen et al. |
| 8,041,436 B2 | 10/2011 | Gao et al. |
| 8,060,340 B2 | 11/2011 | Gao et al. |
| 8,198,840 B2 | 6/2012 | Hexamer |
| 8,467,888 B2 | 6/2013 | Gahinet et al. |
| 8,648,556 B2 | 2/2014 | Lejeune et al. |
| 8,710,777 B2 | 4/2014 | Tian |
| 8,786,230 B2 | 7/2014 | Lee et al. |
| 8,796,974 B2 | 8/2014 | Wang et al. |
| 8,831,755 B2 * | 9/2014 | Bensoussan ............ G05B 5/01 700/28 |
| 9,041,337 B2 | 5/2015 | Tian |
| 9,191,871 B2 * | 11/2015 | Miklos ................. H04W 36/12 |
| 9,720,387 B2 * | 8/2017 | Gao ..................... G05B 13/024 |
| 2002/0103055 A1 * | 8/2002 | Tani ..................... F02D 41/042 477/115 |
| 2003/0199997 A1 | 10/2003 | Gao |
| 2006/0221492 A1 | 10/2006 | Park et al. |
| 2014/0055065 A1 | 2/2014 | Suel et al. |
| 2014/0379102 A1 | 12/2014 | Tian et al. |
| 2015/0329317 A1 | 11/2015 | Agirman et al. |
| 2016/0033944 A1 | 2/2016 | El-Shaer et al. |
| 2017/0063269 A1 * | 3/2017 | Miklosovic ............ H02P 23/14 |

OTHER PUBLICATIONS

Kang, et al., "Online Detection and Suppression of Mechanical Resonance for Servo System", 2012 Third International Conference on Intelligent Control and Information Processing, Jul. 15-17, 2012—Dalian, China. Retrieved on Oct. 20, 2016, 6 pages.

* cited by examiner

SPEED PLANT TRANSFER FUNCTION

RESONANCE TRANSFER FUNCTION

SMOOTHED RESONANCE TRANSFER FUNCTION

METHOD FOR AUTOMATICALLY IDENTIFYING RESONANCE

TECHNICAL FIELD

This disclosure generally relates to motion control, and, more specifically, to estimation of resonance in a controlled mechanical system.

BACKGROUND

Many automation applications employ motion control systems to control machine position and speed. Such motion control systems typically include one or more motors or similar actuating devices operating under the guidance of a controller, which sends position and speed control instructions to the motor in accordance with a user-defined control algorithm. Some motion control systems operate in a closed-loop configuration, whereby the controller instructs the motor to move to a target position or to transition to a target velocity (a desired state) and receives feedback information indicating an actual state of the motor. The controller monitors the feedback information to determine whether the motor has reached the target position or velocity, and adjusts the control signal to correct errors between the actual state and the desired state.

Designers of motion control systems seek to achieve an optimal trade-off between motion speed and system stability. For example, if the controller commands the motor to transition a mechanical component to a target position at a high torque, the machine may initially close the distance between the current position and the desired position at high speed (and thus in a time-efficient manner), but is likely to overshoot the desired position because of the high torque. Consequently, the controller must apply a corrective signal to bring the machine back to the desired position. It may take several such iterations before the motion system converges on the desired position, resulting in undesired machine oscillations. Conversely, instructing the motor to move at a lower torque may increase the accuracy of the initial state transition and reduce or eliminate machine oscillation, but will increase the amount of time required to place the machine in the desired position. Ideally, the controller gain coefficients should be selected to optimize the trade-off between speed of the state transition and system stability. The process of selecting suitable gain coefficients for the controller is known as tuning.

The response of a controlled mechanical system to a signal from a controller having a given set of controller gain coefficients depends on physical characteristics of the mechanical system, including the inertia and friction. Inertia represents the resistance of the motion system to acceleration or deceleration. Friction is a resistive force resulting from the sliding contact between physical components of the system, such as the contact between the rotor and the shaft. Additionally, most mechanical systems include some degree of resonance, which is generally a function of the degree of flexibility between the motor and the load. For example, resonance may be introduced into a mechanical system by the flexibility or compliance between two masses coupled with a flexible media, such as a belt or another flexible coupler. A motion system's resonance may cause instability or degraded motion performance if the controller is not designed to compensate for this resonance, or if the system lacks a suitably configured vibration suppression system. For example, unless accounted for in the control system design, the resonance present in a controlled mechanical system may cause undesired oscillations and noise. The instability caused by the mechanical system's resonance may be especially pronounced at high controller gains.

If the resonance of a motion system is known and characterized, designers can better compensate for this resonance using vibration suppression techniques (e.g., notch filters or other such resonance suppression technologies). However, analysis of a motion system's resonance can be difficult, particularly when low resolution feedback signals are used to measure the motion system's speed.

The above-described is merely intended to provide an overview of some of the challenges facing conventional motion control systems. Other challenges with conventional systems and contrasting benefits of the various non-limiting embodiments described herein may become further apparent upon review of the following description.

SUMMARY

The following presents a simplified summary of one or more embodiments in order to provide a basic understanding of such embodiments. This summary is not an extensive overview of all contemplated embodiments, and is intended to neither identify key or critical elements of all embodiments nor delineate the scope of any or all embodiments. Its purpose is to present some concepts of one or more embodiments in a simplified form as a prelude to the more detailed description that is presented later.

One or more embodiments of the present disclosure relate to systems and methods for estimating the resonance of a controlled mechanical system. To this end, a resonance estimation system is configured to obtain the speed plant transfer function for the mechanical system by applying a torque command signal injected with a defined noise signal, and deriving frequency response data based on the noise-injected torque command signal and the measured speed of the mechanical system in response to the torque command signal. The system then derives resonance information by removing the slow motion dynamics and fast torque control dynamics from the measured speed plant transfer function. Smoothing functions are applied to the resonance frequency response data to remove spikes and obtain relatively smooth gain and phase curves for the resonance. A searching algorithm is then applied to the smoothed frequency response data to determine the locations of the phase peaks in the phase curve. The locations of the phase peaks are used to locate the gain peaks in the gain curve, since these gain peaks are expected to be within the neighborhood of the phase peaks. The locations of these discovered gain peaks correspond to the resonance frequencies, and the amplitudes of the gain peaks correspond to the amplitude of the resonance. Accordingly, the system can analyze the discovered gain peaks in order to characterize the resonance of the mechanical system in terms of the resonance frequencies and/or magnitudes.

By using the peaks of the phase curve as a guide to locating the gain peaks corresponding to system resonances, the resonance estimation system described herein can identify the gain peaks even when analyzing non-ideal gain curves that are degraded by noise, or by low frequency sampling. Thus, the techniques leveraged by the resonance estimation system described herein can obtain accurate measurements of a motion system's resonance frequencies and amplitudes using low-resolution encoders and low sampling rates.

The following description and the annexed drawings set forth herein detail certain illustrative aspects of the one or more embodiments. These aspects are indicative, however, of but a few of the various ways in which the principles of various embodiments can be employed, and the described embodiments are intended to include all such aspects and their equivalents.

DETAILED DESCRIPTION

Figure 1:
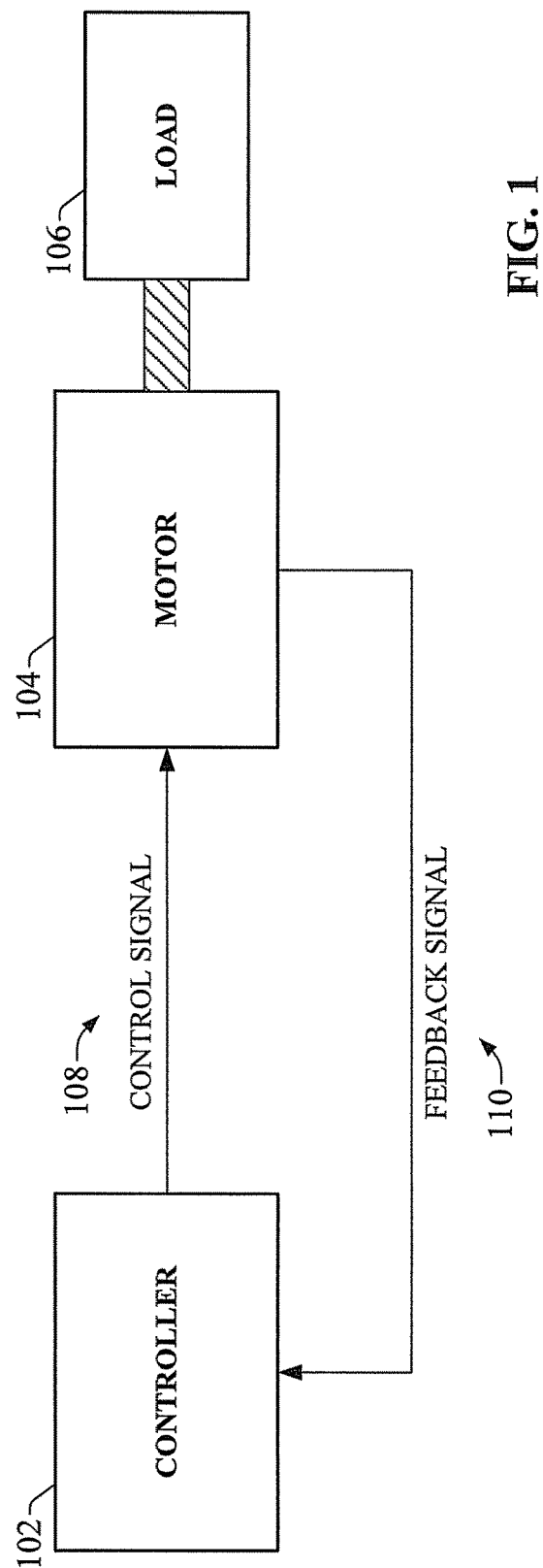
FIG. 1 is a simplified diagram of a closed-loop motion control architecture.

Various embodiments are now described with reference to the drawings, wherein like reference numerals refer to like elements throughout. In the following description, for the purposes of explanation, numerous specific details are set forth in order to provide an understanding of this disclosure. It is to be understood, however, that such embodiments may be practiced without these specific details, or with other methods, components, materials, etc. In other instances, structures and devices are shown in block diagram form to facilitate describing one or more embodiments.

Systems and methods described herein relate to techniques for determining the frequency and amplitude of the resonances of a motion system. According to one or more embodiments, a resonance estimation system can estimate the resonance presence in a motion system without the need for a high-resolution feedback signal or high-frequency sampling. To this end, embodiments of the systems and methods described herein apply signal smoothing procedures that eliminate noise from obtained gain and phase frequency response data for the resonance, and use the location of the peaks in the smoothed phase curve to locate corresponding peaks in the smoothed gain curve, which characterize the frequency and amplitude of the resonances. The systems described herein solve for resonance in part by removing the slow motion dynamics and fast control torque dynamics from the plant transfer function obtained based on measured motor speed data. The resulting resonance information is analyzed to determine the frequency of the phase peak, and to use the location of the phase peak to locate the peak gain, which corresponds to the frequency of resonance mode.

FIG. 1 is a simplified diagram of a closed-loop motion control architecture. Controller 102 is programmed to control motor 104, which drives mechanical load 106. In various example applications, motor 104 may be used to drive an industrial automation application or industrial tool, including but not limited to a machining or material handling robot, a conveyor, a tooling machine, a motorized hand tool, etc. Motor 104 may also be used in the traction and/or propulsion system of an electric vehicle design, including but not limited to an electric or hybrid electric automobile, a bicycles, a forklift or other industrial vehicle, a scooter, a railway vehicle such as a train, or other such vehicles. Motor 104 may also be used in building infrastructure and HVAC (heating, ventilating, and air conditioning) applications that require speed or motion control, such as fans and pumps. Motor 104 may also be used in a home or industrial appliance. For example, motor 104 may be used to drive the drum of a home or industrial washing machine, to control the spinning of a centrifuge, or to control the motion of other such appliances.

Controller 102, motor 104, and load 106 make up the primary components of an example motion control system, wherein linear and/or rotational motion of the load 106 is controlled by motor controller 102. In an example application, load 106 can represent an axis of a single- or multi-axis robot or positioning system. In such applications, controller 102 sends control signal 108 instructing the motor 104 to move the load 106 to a desired position at a desired speed. The control signal 108 can be provided directly to the motor 104, or to a motor drive (not shown) that controls the power delivered to the motor 104 (and consequently the speed and direction of the motor). Feedback signal 110 indicates a current state (e.g., position, velocity, etc.) of the motor 104 and/or load 106 in substantially real-time. In servo-driven systems, feedback signal 110 can be generated, for example, by an encoder or resolver (not shown) that tracks an absolute or relative position of the motor. In sensorless systems lacking a velocity sensor, the feedback signal can be provided by a speed/position estimator. During a move operation, the controller monitors feedback signal 110 to ensure that the load 106 has accurately reached the target position. The controller 102 compares the actual position of the load as indicated by the feedback signal 110 with the target position, and adjusts the control signal 108 as needed to reduce or eliminate error between the actual and target positions.

In another example application, load 106 can represent a spinning load (e.g., a pump, a washing machine, a centrifuge, etc.) driven by motor 104, in which controller 102 controls the rotational velocity of the load. In this example, controller 102 provides an instruction to motor 104 (via control signal 108) to transition from a first velocity to a second velocity, and makes necessary adjustments to the control signal 108 based on feedback signal 110. It is to be appreciated that the resonance estimation techniques of the present application are not limited to use with the example types of motion control systems described above, but rather are applicable for substantially any type of motion control application.

In general, for torque control systems, controller 102 implements torque control that uses a reference torque and current feedback as inputs, and generates a voltage output as the control signal 108. For speed control systems, controller 102 implements speed control that receives a speed reference and speed feedback as inputs, and generates a reference torque for torque control (or a torque current).

Figure 2:
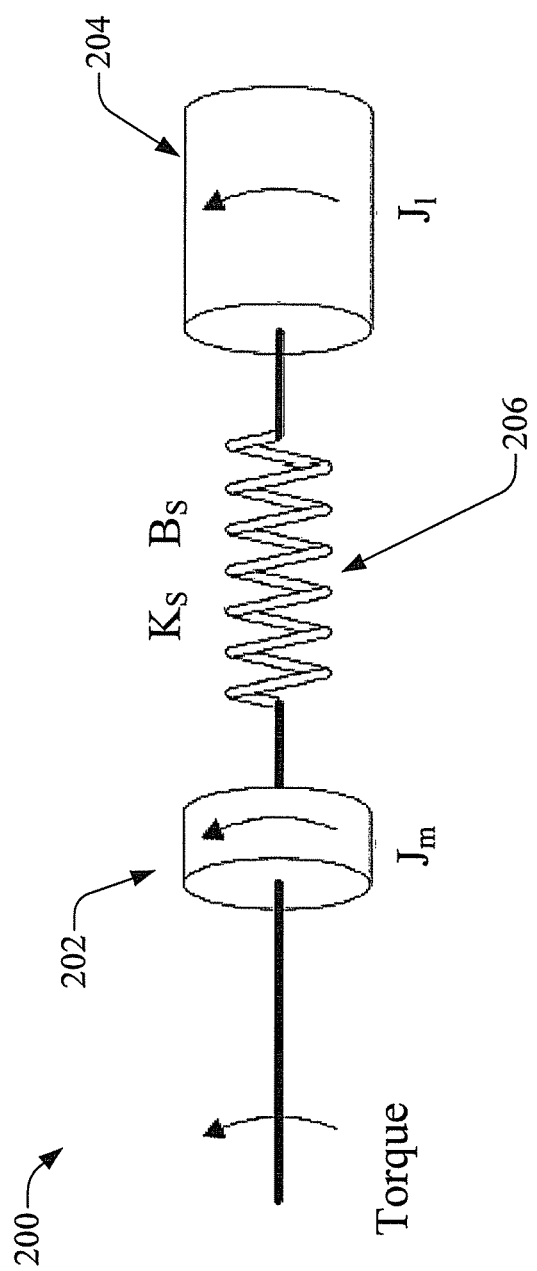
FIG. 2 is a diagram of a simplified model an example industrial motion drive system.

FIG. 2 is a diagram of a simplified model an example industrial motion drive system 200. As depicted in FIG. 2, a drive system can be modeled as a two-inertia system, where the total inertia J comprises inertia $J_m$ of the motor 202 and inertia $J_l$ of the load 204. Mechanical characteristics of the coupling 206 between motor 202 and load 204 are represented by resonance spring constant $K_s$ and resonance damping ratio $B_s$. Thus, in the example system 200, the system gain is the inertia of the system, and the resonant mode of the coupled motor-load configuration is a function of $K_s$ and $B_s$. In real motion systems, the sources of resonance are not limited to the compliance between the motor-load coupling. Rather, resonance can be introduced into the system by flexible couplings between any of the mechanical components of the system.

If the resonance of a controlled mechanical system can be measured and characterized, designers are better able to configure the control system to compensate for these resonances and improve performance of the motion system. For example, if the resonance frequencies and amplitudes are known, a system designer can incorporate a suitably configured notch filter, a low-pass filter, or other vibration suppression mechanism into the motion control design to counteract instabilities caused by the resonance.

Some approaches for detecting and measuring resonance involve frequency response sweeping or noise injection. However, these techniques typically require a high-resolution feedback signal and a high sampling frequency in order to achieve good spectrum analysis, since a low-resolution feedback signal and/or a low sampling frequency may cause the signal to degrade, rendering analysis of the frequency response difficult.

To address these and other issues, embodiments of the resonance estimation system described herein implement resonance detection techniques that can obtain accurate estimates of a motion system's resonance frequency and magnitude without the need for a high-resolution encoder or high sampling frequencies. The resonance estimation system described herein can solve for resonance information by removing the slow motion dynamics and fast torque control dynamics from the measured speed plant transfer function in order to obtain a resonance transfer function. The system then removes noise spikes by applying smoothing functions to this resonance transfer function, yielding relatively smooth gain and phase curves suitable for analysis. A searching algorithm is applied to determine the locations of the phase peaks of the phase curve, and the system uses these phase peak locations as starting points for locating the gain peaks that are expected to be in the neighborhood of the phase peaks. The identified gain peaks correspond to the resonance frequencies for the motion system. This approach allows the gain peaks to be located even when analyzing non-ideal gain curves that are degraded by noise. The techniques leveraged by the resonance estimation system described herein can obtain accurate measurements of a motion system's resonance frequencies and amplitudes using low-resolution encoders—e.g., as low as 4000 counts per revolution—and sampling rates as low as 1 KHz (or possibly lower).

Figure 3:
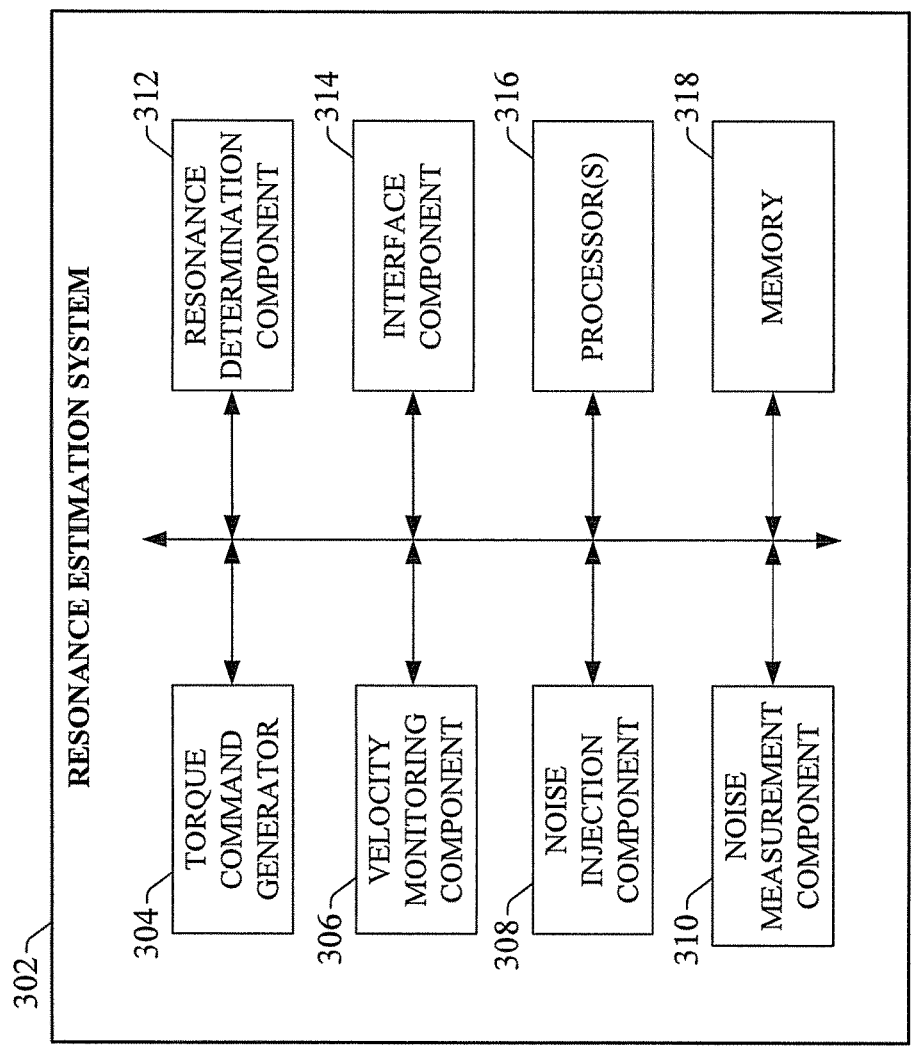
FIG. 3 is a block diagram of an example resonance estimation system capable of generating estimated values of a mechanical system's resonance frequencies and amplitudes.

FIG. 3 is a block diagram of an example resonance estimation system 302 capable of generating estimated values of a mechanical system's resonance frequencies and amplitudes. Resonance estimation system 302 can include a torque command generator 304, a velocity monitoring component 306, a noise injection component 308, a noise measurement component 310, a resonance determination component 312, an interface component 314, one or more processors 316, and memory 318. In various embodiments, one or more of the torque command generator 304, velocity monitoring component 306, noise injection component 308, noise measurement component 310, resonance determination component 312, interface component 314, the one or more processors 316, and memory 318 can be electrically and/or communicatively coupled to one another to perform one or more of the functions of the resonance estimation system 302. In some embodiments, components 304, 306, 308, 310, 312, and 314 can comprise software instructions stored on memory 318 and executed by processor(s) 316. The resonance estimation system 302 may also interact with other hardware and/or software components not depicted in FIG. 3. For example, processor(s) 316 may interact with one or more external user interface device, such as a keyboard, a mouse, a display monitor, a touchscreen, or other such interface devices.

Torque command generator 304 can be configured to output a torque command signal in accordance with a defined routine. Velocity monitoring component 306 can be configured to receive speed data for a motion system for use in determining the resonance of the mechanical system. In some embodiments, the velocity monitoring component 306 can measure and record the speed of the motion system's motor over time in response to the applied torque command signal generated by the torque command generator 304. Alternatively, the velocity monitoring component 306 can receive the measured speed data from separate measuring instrumentation.

Noise injection component 308 can be configured to generate a noise signal for injection into the torque command signal generated by the torque command generator 304. Noise measurement component 310 can be configured to measure a noise level of a speed signal for use as a baseline. This baseline noise level can be used as a basis for the amplitude of the noise injected by the noise injection component 308. The resonance determination component 312 can be configured to analyze the torque and speed data generated or received by the torque command generator 304 and the velocity monitoring component 306 in order to determine the resonance frequencies and amplitudes for the motion system. As will be described in more detail below, the resonance determination component 312 can remove slow motion dynamics and fast torque control dynamics from a speed plant transfer function obtained based on the torque and speed data, yielding resonance frequency response data that is a function of the system's resonance transfer function. Resonance determination component 312 can then apply smoothing functions to this frequency response data to obtain gain and phase curves that can be analyzed for resonance, and apply a searching algorithm to determine the locations of the phase peaks of the phase curve. Resonance determination component 312 can then locate the gain peaks corresponding to the resonance frequencies based on the locations of the phase peaks.

Interface component 314 can be configured to receive user input and to render output to the user in any suitable format (e.g., visual, audio, tactile, etc.). User input can be, for example, user-entered parameters used by the resonance estimation system 302 when executing an estimation sequence (to be described in more detail below). The one or more processors 316 can perform one or more of the functions described herein with reference to the systems and/or methods disclosed. Memory 318 can be a computer-readable storage medium storing computer-executable instructions and/or information for performing the functions described herein with reference to the systems and/or methods disclosed.

Figure 4:
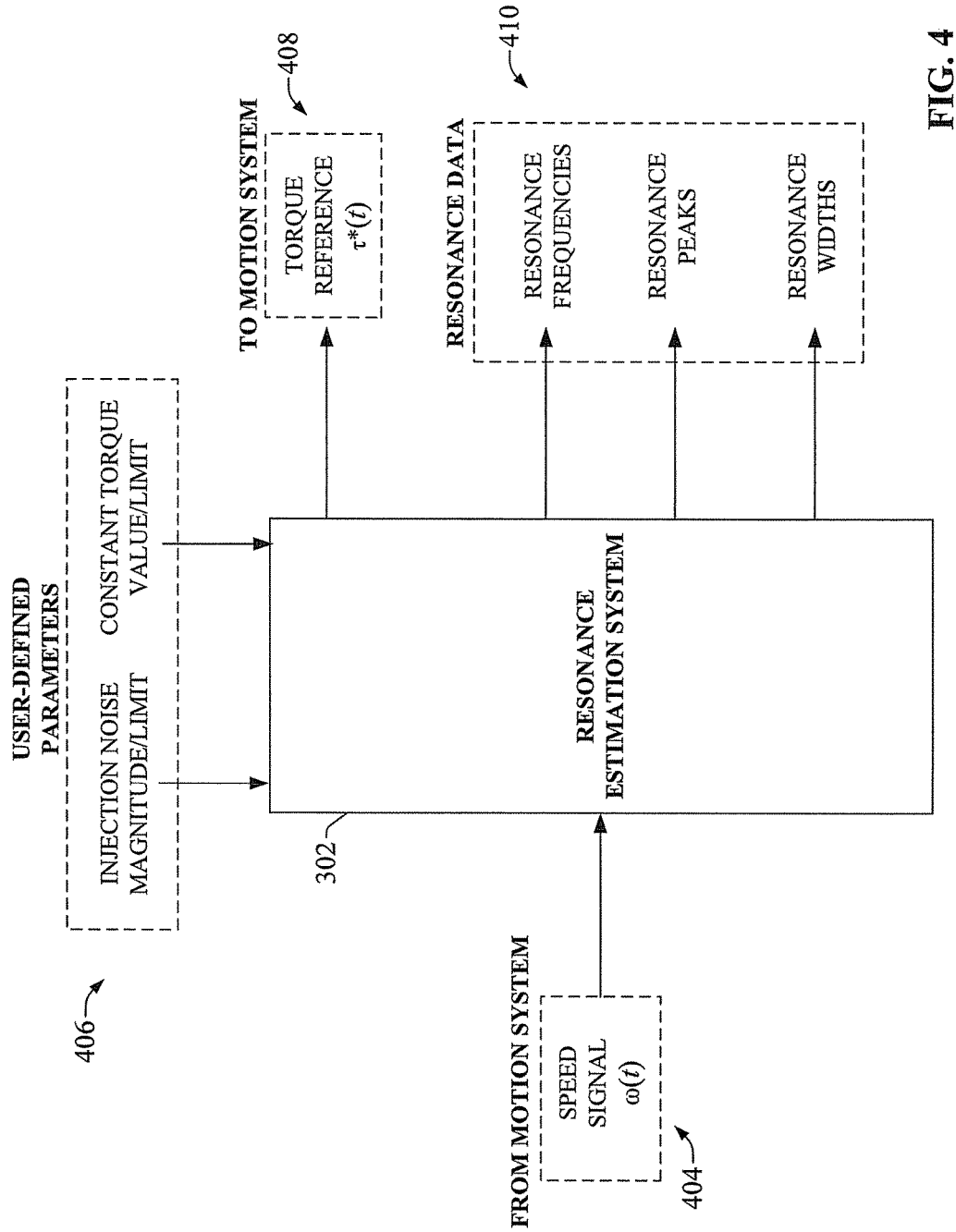
FIG. 4 is a block diagram illustrating the inputs and outputs associated with an example resonance estimation system.

The resonance estimation system 302 can generate estimates for a mechanical system's resonance frequencies and amplitudes by running the system through a testing sequence and calculating the estimates based on the results. FIG. 4 is a block diagram illustrating the inputs and outputs associated with resonance estimation system 302. Resonance estimation system 302 can generate a torque reference signal 408 (e.g., an analog voltage signal such as a 0-10 VDC signal, an analog current signal such as a 4-20 mA signal, a digital signal, a software instruction, or any other suitable type of control signal), which instructs a motor driving the motion system to rotate in a specified direction at a specified torque. During the estimation sequence, the torque reference signal 408 comprises a constant torque command injected with a predefined noise level. In some embodiments, the noise level may be a multiple of a measured baseline noise level for the motion system.

As the motion system responds to the applied torque reference signal 408, a speed signal 404 from the motion control system is provided to the estimation system 302. Speed signal 404 represents the speed of the motion system over time in response to application of torque reference signal 408. When a sufficient amount of speed data has been obtained, resonance estimation system 302 generates resonance data 410 representing estimates of the resonance frequencies, resonance peaks, and/or resonance widths for the motion system. Resonance estimation system 302 determines these estimates based on the torque reference signal 408 that was issued to the motion system and the corresponding measured speed signal 404, using techniques to be described in more detail herein.

Some embodiments of resonance estimation system 302 may also allow users to set one or more configuration parameters 406 for the system 302. For example, in some embodiments, the system 302 may allow users to set a constant torque value to be used for the torque reference signal during the estimation sequence. Alternatively, the system 302 may allow the user to set a maximum torque limit for the constant torque reference. In some embodiments, the system 302 may also allow a user to set an injection noise magnitude value that sets an amplitude of the noise injected into the applied torque signal by the estimation system 302.

Figure 5:
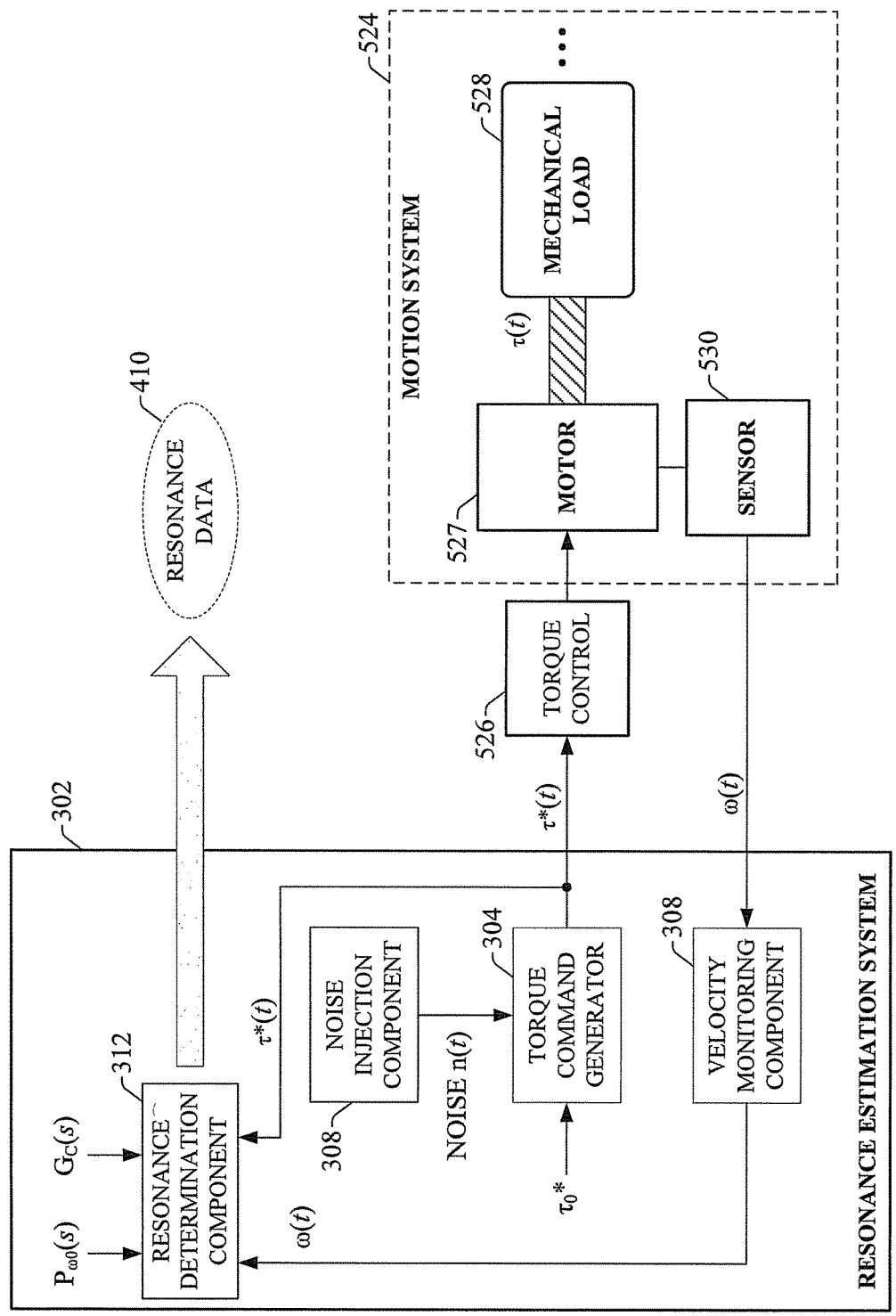
FIG. 5 is a diagram illustrating interactions between a resonance estimation system and a torque control system during an example resonance estimation sequence.

FIG. 5 is a diagram illustrating interactions between resonance estimation system 302 and a torque control system during an example resonance estimation sequence. In this example, motion system 524 comprises one or more mechanical loads 528 (e.g., coupled mechanical masses) whose motion is driven by torque $\tau^*(t)$ applied by motor torque control 526. Motion system 524 may comprise, for example a positioning axis, a rotational component of a machine, a conveyor system, or other such motor-driven loads. A sensor 530 or estimator is used to measure the speed of the motor 527 and to generate a corresponding speed signal $\omega(t)$ that serves as feedback to resonance estimation system 302.

In some embodiments, resonance estimation system 302 can be an integrated component of a controller that generates and outputs torque reference signals to torque control 526 to facilitate programmed control of motion system 524. Such a controller may execute a control program that regulates the torque reference signal based on a desired target torque or speed (dictated by the control program), and, in the case of speed control, the motor speed feedback measured by the sensor 530 (or estimator). In such embodiment, resonance estimation system 302 can be a functional component of the controller's operating system and/or control software executed by one or more processors residing on the controller. Resonance estimation system 302 can also be a hardware component residing within the controller, such as a circuit board or integrated circuit, that exchanges data with other functional elements of the controller. Other suitable implementations of resonance estimation system 302 are within the scope of one or more embodiments of the present disclosure. The controller itself may be a hardware controller, such as a programmable logic controller, motor drive, or other type of hardware controller. The controller may also be a system-on-chip or other type of silicon-based or microchip controller in some implementations.

In other embodiments, resonance estimation system 302 may be a separate system from the controller. For such embodiment, resonance estimation system 302 can exchange data with the controller or other elements of the torque control system via any suitable communications means, including but not limited to wired or wireless networking, hardwired data links, or other communication means.

The sequence carried out by the resonance estimation system 302 to determine the resonances present in motion system 524 comprises four general steps. First, a noise level of the motion system's speed signal 404 is measured and recorded as a baseline noise value. Second, noise injection component 308 injects a noise signal n(t) into a constant torque reference $\tau_0^*$ to yield torque reference signal $\tau^*(t)$. In the case of closed-loop speed control systems, the constant torque reference $\tau_0^*$ can be generated by a speed controller, which provides the torque reference to a torque control system to be translated to actual torque $\tau(t)$ applied to the motion system. The amplitude of the noise signal n(t) is set to be a multiple n of the baseline noise level previously measured from the speed signal. In some embodiments, the estimation system 302 can allow the multiple n to be set by the user, allowing a degree of manual control over the amount of noise injected into the torque reference signal. The motor speed $\omega(t)$ as a function of time resulting from application of the noise-injected torque reference signal is measured or otherwise received by the velocity monitoring component 308. The torque reference data $\tau^*(t)$ and the speed data $\omega(t)$ are provided to the resonance determination component 312, which uses this information to generate frequency response data for the motion system 524. Third, the resonance determination component 312 removes the known slow dynamics of the motion and the fast torque dynamics from the measured frequency response data. The information that remains is taken to be the resonance information for the motion system. The second and third steps can be repeated multiple times, and the results averaged in order to obtain average resonance information. Averaging the resonance information in this manner may yield more accurate results. Finally, resonance determination component 312 applies smoothing functions to the resonance information, and uses a searching algorithm to obtain the resonance frequencies, amplitudes, and/or widths for the motion system. The resonance determination component 312 uses the locations (frequencies) of the phase curve peaks to assist in locating the peaks of the gain curve, which correspond to the resonance frequencies. These steps are described in more detail below.

Observations that serve as a basis for the resonance estimation techniques described herein are now discussed. The Laplace transform maps a time domain function to a function of the complex variable $$s = \sigma + j\omega \tag{1}$$

If the real component $\sigma=0$, the Laplace transform becomes a Fourier transform. For simplicity, the complex number frequency parameter s is used in this disclosure to represent the frequency domain parameter $j\omega$ in the context of frequency response.

Figure 6:
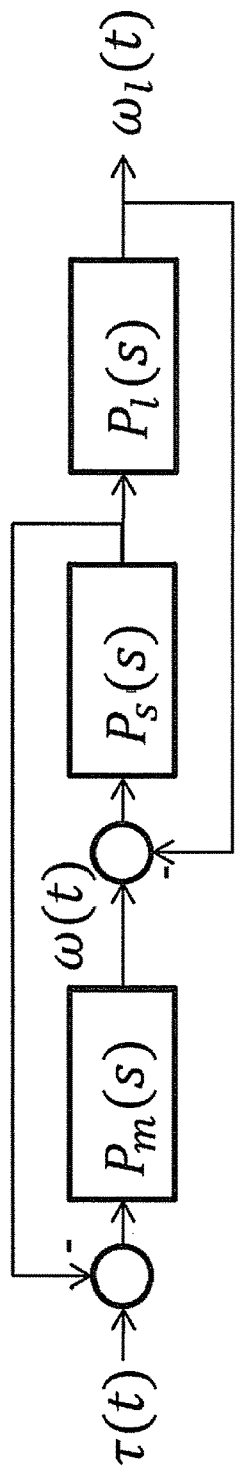
FIG. 6 is a diagram that models a motion system with resonance.

FIG. 6 is a diagram that models a motion system with resonance. The motor side, load side, and coupling transfer functions describing the system are as follows:

$$P_m(s) = \frac{1}{J_m s + B_m} \tag{2}$$

$$P_l(s) = \frac{1}{J_l s + B_l} \tag{3}$$

$$P_s(s) = B_s + \frac{K_s}{s} \tag{4}$$

Where $P_m(s)$ is the motor-side plant transfer function, $P_l(s)$ is the load-side plant transfer function, $P_s(s)$ is the motor-load coupling transfer function, $J_m$ Is the motor inertia, $B_m$ is the motor viscous friction coefficient, $J_l$ is the load inertia, $B_l$ is the load viscous friction coefficient, $B_s$ is the resonance damping ratio, and $K_s$ is the resonance spring constant.

From equations (2), (3), and (4), the plant transfer function from motor torque to motor speed, referred to as the speed plant transfer function $P_\omega(s)$, can be derived as:

$$P_\omega(s) = \frac{J_l s^2 + (B_l + B_s)s + K_s}{J_m J_l s^3 + (B_m J_l + B_l J_m + (J_l + J_m)B_s)s^2 + (B_m B_l + (J_l + J_m)K_s + (B_l + B_m)B_s)s + (B_l + B_m)K_s} \tag{5}$$

By rewriting equation (5), it can be seen that the speed plant transfer function $P_\omega(s)$ comprises slow dynamics with a resonance:

$$P_\omega(s) = \frac{1}{J_t s + B_t} \cdot \frac{b_2 s^2 + b_1 s + K_s}{a_2 s^2 + a_1 s + K_s} \tag{6}$$

where $$J_t = J_m + J_l \tag{7}$$

$$B_t = B_m + B_l \tag{8}$$

and $a_1$, $a_2$, $b_1$, and $b_2$ are coefficients of the resonance transfer function.

In equation (6), the first term represents the slow dynamics transfer function, and the second term represents the resonance transfer function, as given by the definitions:

$$P_{\omega 0}(s) = \frac{1}{J_t s + B_t} \tag{9}$$

$$R(s) = \frac{b_2 s^2 + b_1 s + K_s}{a_2 s^2 + a_1 s + K_s} \tag{10}$$

where $P_{\omega 0}(s)$ is the speed plant slow dynamics transfer function, and $R(s)$ is the resonance transfer function. Substituting equations (9) and (10) into equation (6) yields $$P_\omega(s) = P_{\omega 0}(s)R(s) \tag{11}$$

In the special case used in resonance analysis, motor and load viscous friction coefficients are assumed to be zero ($B_m = B_l = 0$), which yields a speed plant slow dynamics transfer function given by:

$$P_{\omega 0}(s) = \frac{1}{J_t s} \tag{12}$$

and a resonance transfer function given by:

$$R(s) = \frac{\frac{J_l}{k_s}s^2 + B_s s + K_s}{\frac{J_l J_m}{J_l + J_m}s^2 + B_s s + K_s} \tag{13}$$

Considering the torque control dynamics, the speed plant transfer function is then defined as:

$$P_\omega(s) = P_{\omega 0}(s)R(s)G_c(s) \tag{14}$$

where $G_c(s)$ is the torque control closed-loop transfer function, which represents the motor torque generation with respect to the torque reference.

Motor and load frictions are non-zero in real applications. It can be difficult to obtain the coefficients as functions of motion parameters $J_m$, $J_l$, $B_m$, $B_l$, $B_s$, and $K_s$ using an analytic approach. However, there will be a resonance, as can be seen from the analysis of the plant transfer function.

Figure 7:
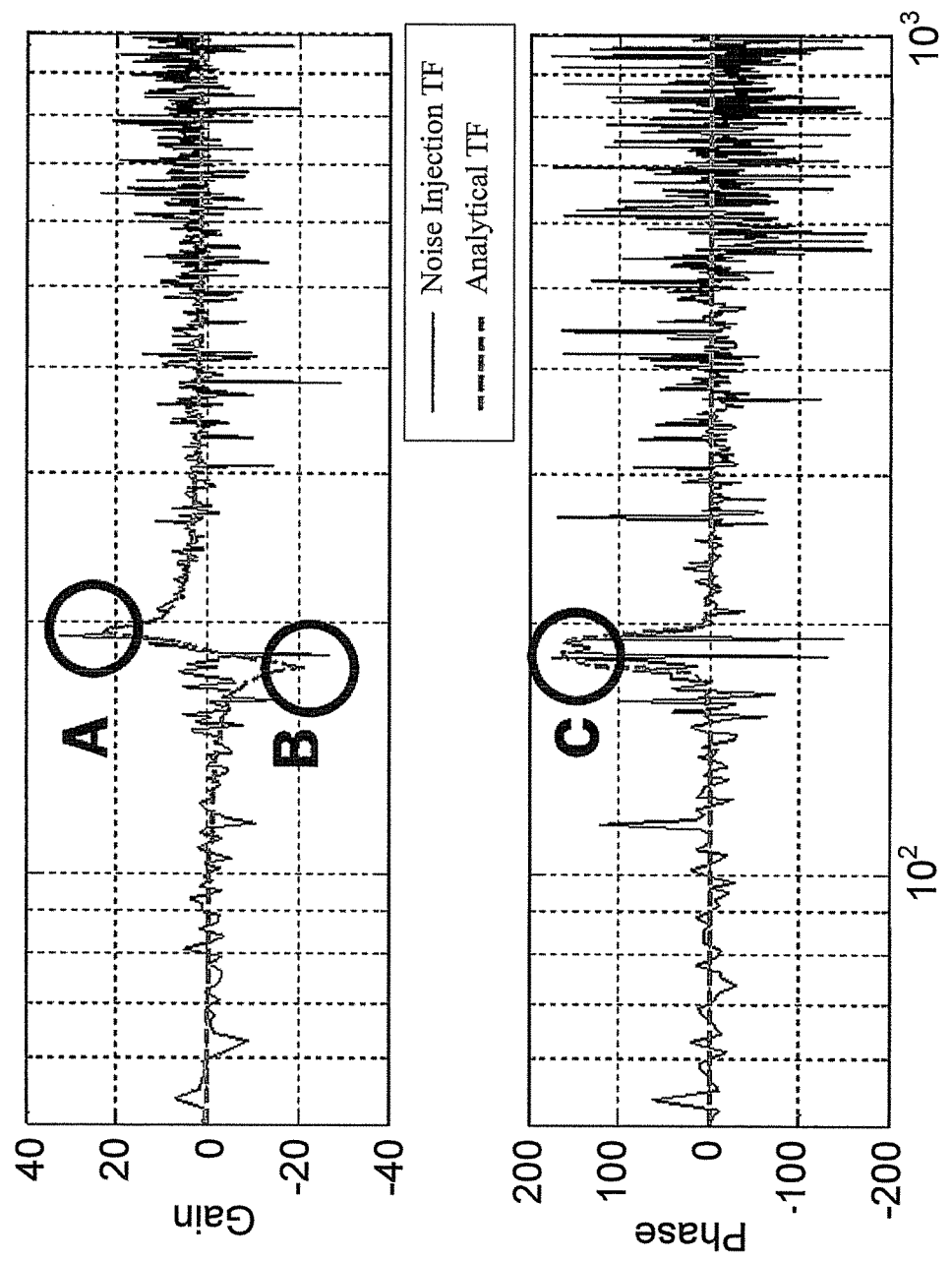
FIG. 7 is a Bode plot of an example resonance transfer function.

FIG. 7 is a Bode plot of an example resonance transfer function. The clean dashed curve is the analytical transfer function Bode, and the spiky solid curved is the Bode obtained through simulation with noise injection. Point B on the Bode gain plot is the anti-resonance, at which frequency the gain of the curve reaches minimum. Point A on the Bode gain plot is the resonance, at which frequency the gain of the curve reaches maximum. Point C on the Bode phase plot is the frequency at which the phase reaches maximum, and is located between points A and B.

From FIG. 7, it can be seen that high level of noise makes the anti-resonance at point B difficult to detect. However, analysis suggests that the phase peak (point C) is a reliable point from which to assess the neighborhood of a resonance.

In particular, the resonance frequency corresponding to the gain peak at point A will be slightly higher than the frequency of the phase peak at point C. The resonance estimation system 302 described herein leverages this phase peak in order to determine the resonance of the system, as will be described below.

The torque dynamics need to be fast enough to provide a commanded torque reference from the speed control. Therefore, controllers that implement torque control are typically configured for higher bandwidth relative to controllers that implement speed control. The torque control closed-loop transfer function $G_c(s)$ is typically known. $G_c(s)$ appears as part of the speed control plant, together with the motion plant $P_\omega(s)$. The speed controller transfer function $C_\omega(s)$ is determined given the controller parameters.

The resonance estimation techniques described herein assume the slow motion dynamics given by $P_{\omega 0}(s)$ are known. These slow motion dynamics can be obtained using any suitable method. For example, U.S. patent application Ser. No. 14/851,308 discloses a system that estimates inertia and viscous friction for controlled mechanical systems by applying a stable torque reference to accelerate and decelerate a motor, and estimating the inertia and viscous friction coefficient based on the time-varying torque reference and the corresponding measured velocity curve. Since the estimation technique described in that reference uses a stable torque reference to accelerate and decelerate motor speed without exciting resonance of the system, that technique can be used to obtain the slow motion dynamics for the motion system. The entirety of U.S. patent application Ser. No. 14/851,308 is incorporated herein by reference. With the slow motion dynamics known, the resonance estimation system 302 can remove these slow motion dynamics from measured frequency response data for the motion system in order to obtain resonance frequency response data.

As noted above, as a first step of the resonance estimation sequence, the resonance estimation system 302 measures the noise level present in the speed signal $\omega(t)$ received from the motion system 524. To this end, torque command generator 304 can output a constant torque reference signal (without noise injection), and the velocity monitoring component 308 can measure the resulting speed signal $\omega(t)$. When the speed signal has reached a steady state, the noise measurement component 310 can determine a level of noise present in the speed signal. This noise level is used by resonance estimation system 302 as a baseline to set a level of noise to be injected into the torque reference $\tau^*(t)$ by the noise injection component 308. In some embodiments, the level of injected noise can be set to be a multiple of the baseline noise level of the measured speed signal without noise injection, such that the noise injected by the noise injection component 308 is n times the baseline level.

During this baseline noise measurement step, the torque command generator 304, velocity monitoring component 308, and noise measurement component 310 can continue applying a constant torque reference $\tau^*(t)$ and measuring the resulting speed signal $\omega(t)$ until system 302 has determined a baseline noise level present in the speed signal to a sufficient degree of accuracy. In an example technique for determining the baseline noise level, after the motion system has accelerated and achieved a steady-state speed in response to the constant torque reference $\tau^*(t)$, noise measurement component 310 may measure the average amplitude of variations in the speed signal $\omega(t)$ over a defined period of time. Upon expiration of the defined time duration, the average amplitude can be taken as the baseline noise. In another example technique, after the motion system 524 has reached steady state, the noise measurement component 310 can measure the average amplitude of the variations in the speed signal until the average settles to a substantially constant value, which is taken to be the baseline noise level. Other techniques for determining the baseline noise level in the speed signal are also within the scope of one or more embodiments of this disclosure.

Once the baseline noise level determined, the resonance estimation system 302 proceeds to the second step of the estimation sequence. As shown in FIG. 5, the noise injection component 308 injects predefined noise n(t) into the constant torque reference to yield torque reference $\tau^*(t)$, which is output to the control system as a reference signal by torque command generator 304. As the torque reference signal $\tau^*(t)$ is being output, the velocity monitoring component 308 measures the resulting speed signal $\omega(t)$ over a time duration. The time duration during which the noise-injected torque reference signal $\tau^*(t)$ is sent to the system and the corresponding motor speed $\omega(t)$ is measured can be set to any suitable duration that allows a sufficient amount of time-varying speed data to be collected for calculation of the speed plant transfer function for the motion system. In some embodiments, rather than measuring the speed data for a predefined time duration, the system 302 may continue applying the torque reference and obtaining measured speed data until a defined condition is met, where the defined condition is an indication that a sufficient amount of data has been collected for generation of the motion system's frequency response. At the conclusion of this data collection step, based on the applied noise-injected torque reference $\tau^*(t)$ and the resulting speed signal $\omega(t)$, the resonance determination component 312 generates frequency response data for the motion system 524, which is a function of the speed plant transfer function $P_\omega(s)$ of the motion system together with the closed-loop torque control transfer function.

Figure 8:
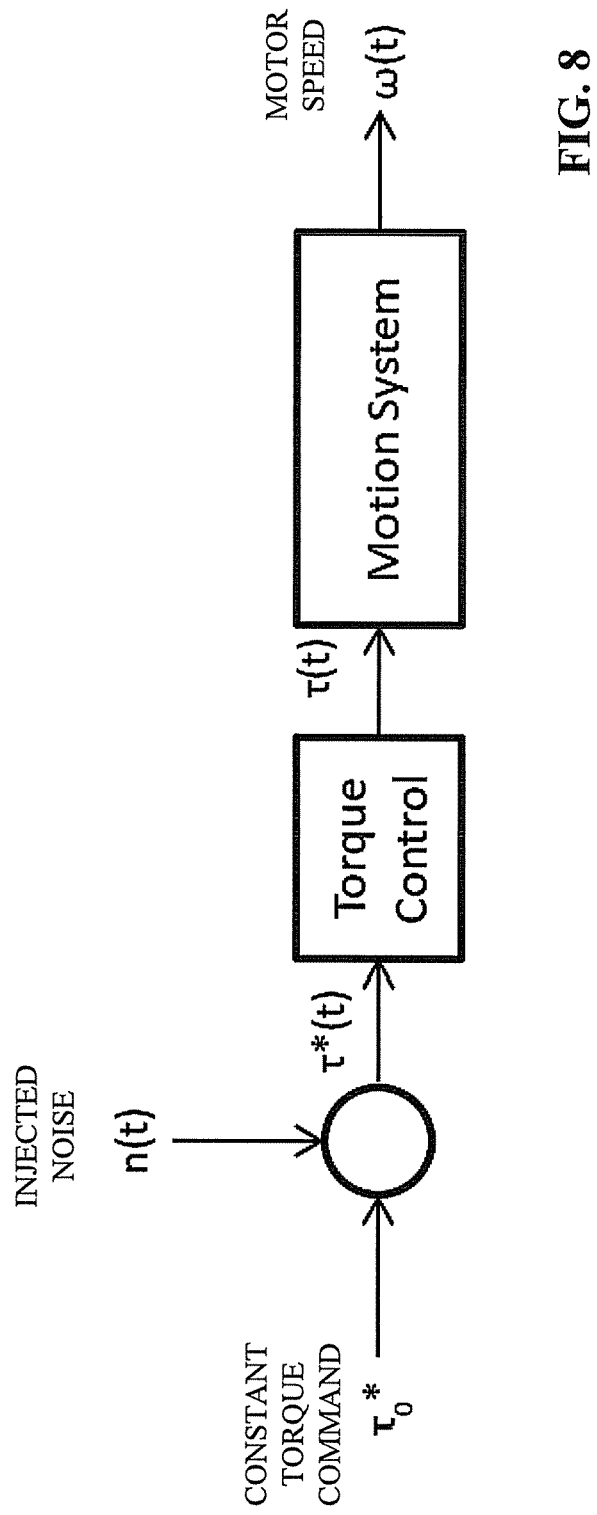
FIG. 8 is a diagram that models an open-loop torque control system with noise injection.

The manner in which resonance estimation system 302 determines the frequency response depends on whether the motion control system performs torque control or speed control. Estimation of resonance in the torque control scenario is now discussed. FIG. 8 is a diagram that models an open-loop torque control system with noise injection. In the open-loop torque control manner, the injected noise n(t) is added to a constant torque value $\tau_0^*$ to yield the torque reference $\tau^*(t)$. This torque reference $\tau^*(t)$ is provided to a torque controller, which produces an actual motor torque $\tau(t)$ on the motion system that results in a corresponding motor speed $\omega(t)$.

Figure 9:
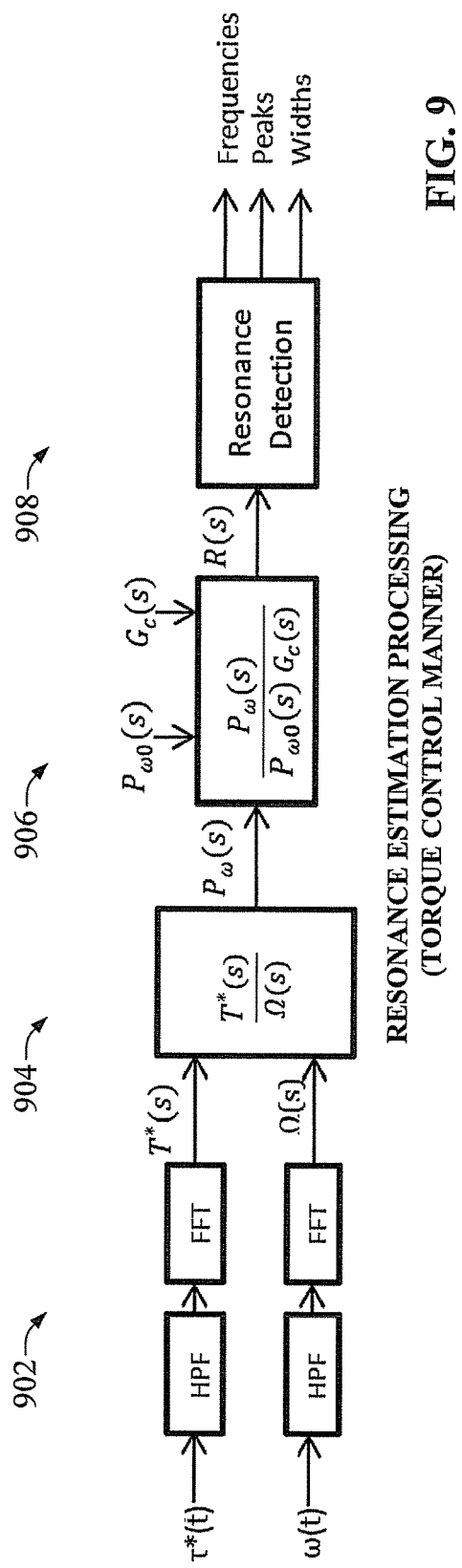
FIG. 9 is a block diagram illustrating processing performed on a torque reference and motor speed by a resonance determination component in a torque control scenario.

FIG. 9 is a block diagram illustrating the processing performed on the torque reference $\tau^*(t)$ and motor speed $\omega(t)$ by the resonance determination component 312 in the torque control scenario. The torque reference $\tau^*(t)$ is provided to the resonance determination component 312, which high-pass filters the torque data and applies a fast Fourier transform to the resulting filtered data at 902 in order to obtain $T^*(s)$, which is the Laplace transform of $\tau^*(t)$. Likewise, the measured motor speed $\omega(t)$ is provided to the resonance estimation component 312, which high-pass filters the speed data and applies a Fourier transform to the resulting filtered data in order to obtain $\Omega(s)$, which is the Laplace transform of $\omega(t)$.

For the torque control scenario, the speed plant transfer function is then obtained at 904 by:

$$P_\omega(s) = \frac{T^*(s)}{\Omega(s)} \tag{15}$$

Once the speed plant transfer function given by equation (15) is obtained, the resonance estimation component 312 proceeds to the third step by removing the speed plant slow dynamics transfer function $P_{\omega 0}(s)$, as well as the torque (current q-axis) closed-loop transfer function $G_c(s)$, from the speed plant transfer function $P_\omega(s)$ at 906. The speed plant slow dynamics transfer function $P_{\omega 0}(s)$ represents the slow dynamics from motor/load inertia and friction. In this example it is assumed that the speed plant slow dynamics are known, or can be obtained via measurement. For example, speed plant slow dynamic transfer function may be given by equation (9) above, and may be derived using any suitable technique (e.g., using the inertia and viscous friction estimation technique disclosed in U.S. patent application Ser. No. 14/851,308). The torque closed-loop transfer function $G_c(s)$ represents the fast torque control dynamics, and is also assumed to be known. Removing the speed plant slow dynamics represented by transfer function $P_{\omega 0}(s)$ and the fast torque control dynamics represented by torque closed-loop transfer function $G_c(s)$ from the speed plant transfer function $P_\omega(s)$ yields the resonance transfer function R(s) for the motion system, which can be given by:

$$R(s) = \frac{P_\omega(s)}{P_{\omega 0}(s) G_c(s)} \quad (16)$$

Figure 10:
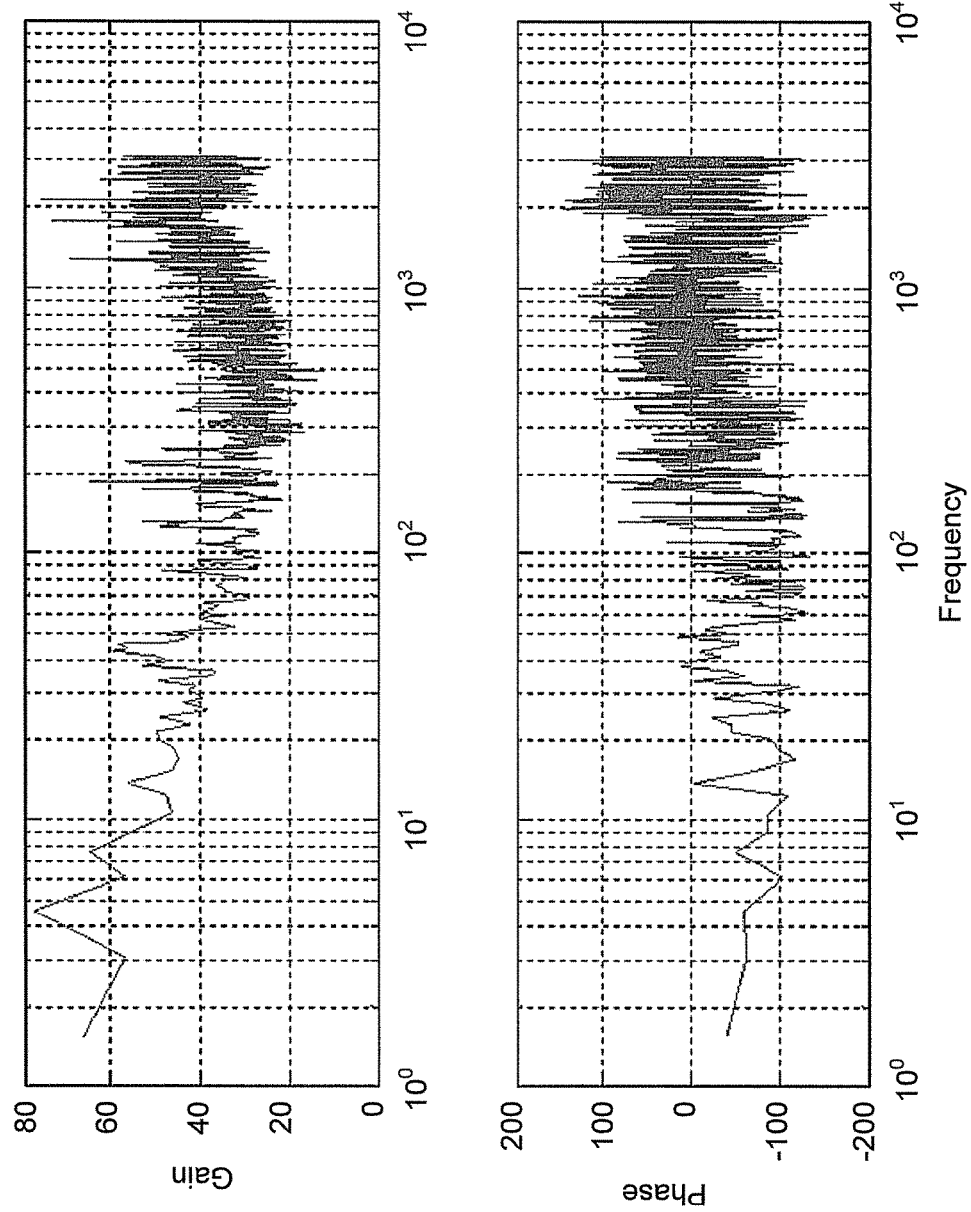
FIG. 10 is an example Bode plot of the speed plant transfer function prior to removal of slow dynamics and fast dynamics.
Figure 11:
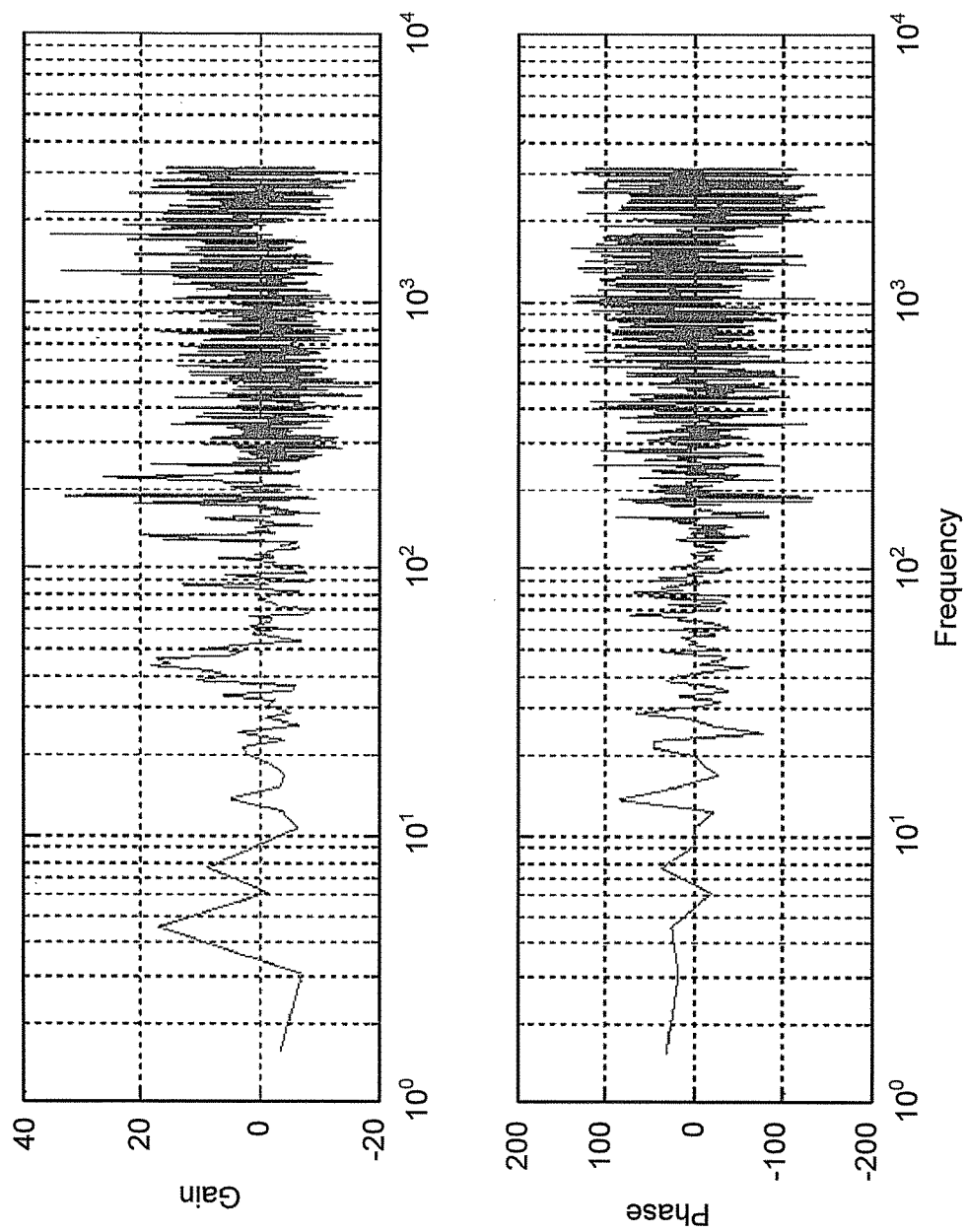
FIG. 11 is an example Bode plot of a resonance transfer function obtained by removing the slow and fast dynamics from a speed plant transfer function.

FIG. 10 is an example Bode plot of the speed plant transfer function $P_\omega(s)$ prior to removal of the slow dynamics and fast dynamics, obtained from actual motion data $\tau^*(t)$ and $\omega(t)$. FIG. 11 is an example Bode plot of the resonance transfer function R(s) obtained by removing the slow and fast dynamics from the speed plant transfer function of FIG. 10 (step 906 in FIG. 9). In some embodiments, the steps of injecting noise n(t) into torque reference signal and measuring the resulting motor speed feedback to determine the speed plant transfer function (the second step of the resonance estimation process), and removing the slow dynamics of the motion and the fast torque control dynamics from the measured data to obtain the resonance information (the third step of the resonance estimation process) can be repeated by system 302 multiple times, and the resonance information obtained via each iteration of the second and third steps can be averaged in order to obtain average resonance information. Using the average resonance information obtained from multiple iterations of the second and third steps described above can yield more accurate results relative to using the results of only one iteration.

Once the resonance transfer function is obtained in accordance with the second and third steps described above, the system 302 proceeds to the fourth step of the resonance estimation process (908 in FIG. 9), in which smoothing functions are applied to the resonance frequency response data and a searching algorithm is applied to the resulting smoothed frequency response data to identify the resonance information for the motion system. The smoothing functions can render the data more conducive to analysis, since the resonance frequency response data obtained by removing the slow and fast dynamics from the speed plant transfer function as described above may include undesired data spikes resulting from measurement noise or other factors. Therefore, to prepare the resonance frequency response data for further analysis, after the resonance frequency response information is obtained as described above, the resonance determination component 312 smooths the data by applying a series of functions that remove single spikes from the frequency response data, as well as spikes in the neighboring areas, in order to obtain smooth resonance gain and phase curves. The smoothing functions applied by the resonance determination component 312 are based on an assumption that neither of the gain or phase curves should include a single frequency point spike with a large amplitude. Rather, valid peaks will typically have a degree of width encompassing a range of contiguous frequencies. Accordingly, in some embodiments, the smoothing functions can be configured to identify and remove isolated data spikes found at single frequency points that have magnitudes that exceed a threshold magnitude. This technique is only intended to be exemplary, and it is to be understood that any suitable smoothing method can be applied by system 302 in order to yield relatively clean resonance information suitable for subsequent analysis. In some embodiments, spikes to be removed from the resonance frequency data can be identified based on a comparison of the gain and phase curves of the resonance Bode plot. For example, if a single-frequency spike in either of the gain or phase curve does not have a corresponding spike in the other curve, the system may remove the spike as unwanted noise.

Figure 12:
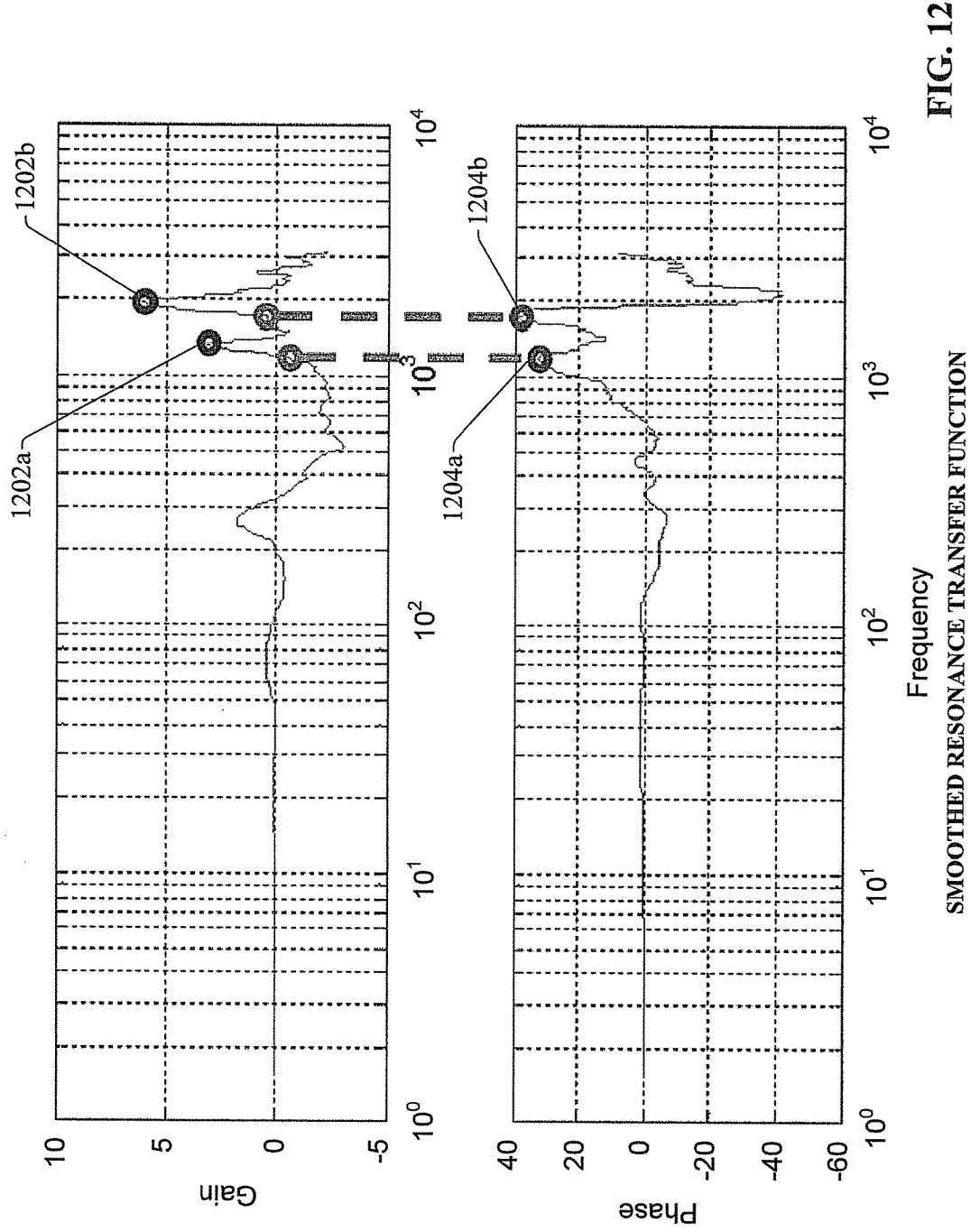
FIG. 12 is an example plot of a resonance Bode after smoothing functions have been applied by a resonance determination component.

FIG. 12 is an example plot of the resonance Bode of FIG. 11 after the smoothing functions have been applied by the resonance determination component 312. In this illustrated example, the motion system from which this data was obtained contains two resonances, as identified by the two peaks 1202a and 1202b in the gain curve. To identify these resonances, the resonance determination component 312 applies a searching algorithm to the smoothed resonance frequency response data. The searching algorithm first searches the phase curve, starting at a low frequency and searching through higher frequencies, in order locate the peaks in the phase curve. In the example depicted in FIG. 12, two phase peaks 1204a and 1204b are discovered by the searching algorithm. As noted above in connection with FIG. 7, the gain peaks corresponding to resonance frequencies will typically be found at frequencies slightly higher than (i.e., in the neighborhood to the right of) the phase peaks. Accordingly, for each discovered phase peak 1204, the searching algorithm leverages the frequency location of the phase peak to locate the corresponding gain peak in the frequency neighborhood to the right of the phase peak 1204.

For example, based on the discovered location of the first phase peak 1204a, the searching algorithm executed by the resonance determination component 312 can search the gain curve, beginning the search at the frequency corresponding to the phase peak 1204a and proceeding through increasingly higher frequencies in the neighborhood to the right of the phase peak frequency (e.g., within a defined frequency range to the right of the phase peak frequency), until a peak is discovered in the gain curve. The searching algorithm can be configured to use any suitable criteria for identifying the peak in the gain curve in the neighborhood to the right of the phase peak frequency (e.g., identifying a local maximum in the gain curve to the right of the phase peak frequency, or another technique for recognizing presence of a peak). Likewise, the resonance determination component 312 will discover the location of the second gain peak 1202b based on the frequency corresponding to the second phase peak 1204b in a similar manner. The frequencies corresponding to the discovered gain peaks 1202a and 1202b are taken to be the resonance frequencies for the motion system, and the amplitudes of the gain peaks 1202a and 1202b are taken to be the magnitudes of the resonances.

With the locations of the resonances located in the gain curve, the resonance determination component 312 can then apply any suitable analysis on the portions of the gain curve in the neighborhood of the discovered gain peaks 1202a and 1202b in order to determine the frequencies, magnitudes, and widths (frequency range) of the resonances. In this way, the resonance estimation system 302 can sufficiently characterize the resonance(s) of the motion system, so that suitable countermeasures can be designed for suppressing the resonance of the motion system. For example, the identified resonance information can be used to design or select a suitable notch filter or other vibration suppression component capable of attenuating or eliminating the effects of the resonance.

The foregoing example described the steps carried out by the resonance estimation system 302 in the torque control scenario. These resonance identification techniques can also be performed for motion control systems that perform speed control. While the steps for removing slow and fast dynamics from the plant transfer function, smoothing the resonance data, and analyzing the smoothed data to determine the resonance information for the speed control case are substantially the same as in the torque control case, the techniques for injecting noise into the reference signal and obtaining the speed plant transfer function are adapted for speed control systems.

Figure 13:
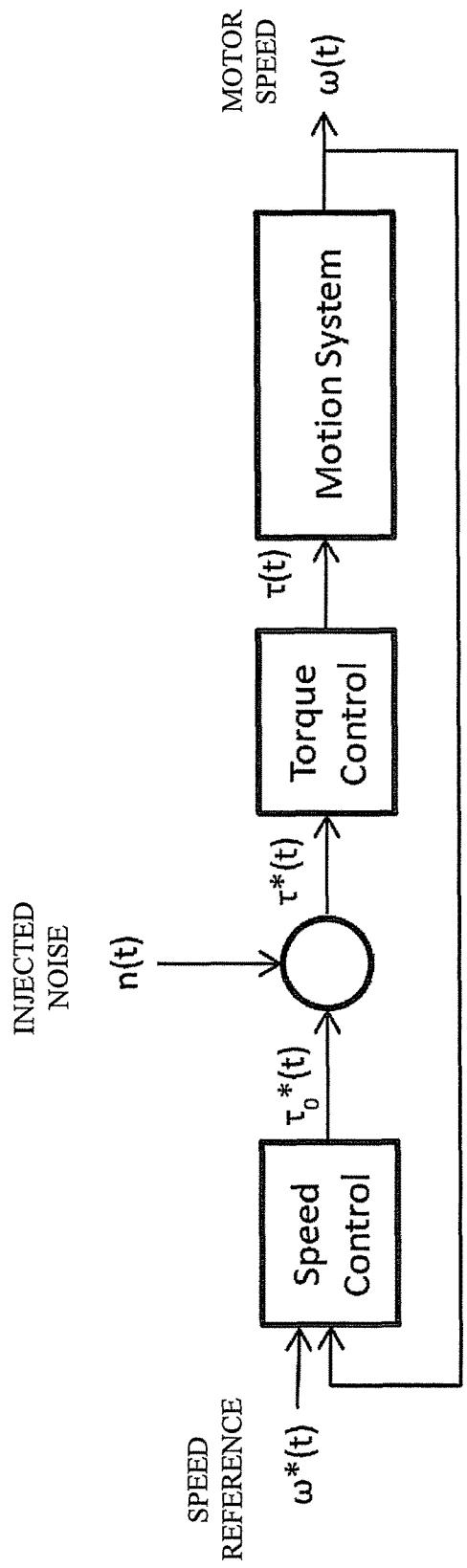
FIG. 13 is a diagram that models a closed-loop speed control system with noise injection.

FIG. 13 is a diagram that models a closed-loop speed control system with noise injection. In the speed control case, after the baseline noise level of the speed signal without noise injection is determined (the first step of the resonance estimation procedure), the speed reference $\omega^*(t)$ is set to a constant value, causing the speed control to generate a corresponding torque command $\tau_0^*(t)$ for achieving the constant speed. The torque command $\tau_0^*(t)$ generated from speed control is injected with noise n(t) by the noise injection component 308 to yield a torque reference $\tau^*(t)$, which is translated by the torque control to an actual motor torque $\tau(t)$ applied to the motion system.

Figure 14:
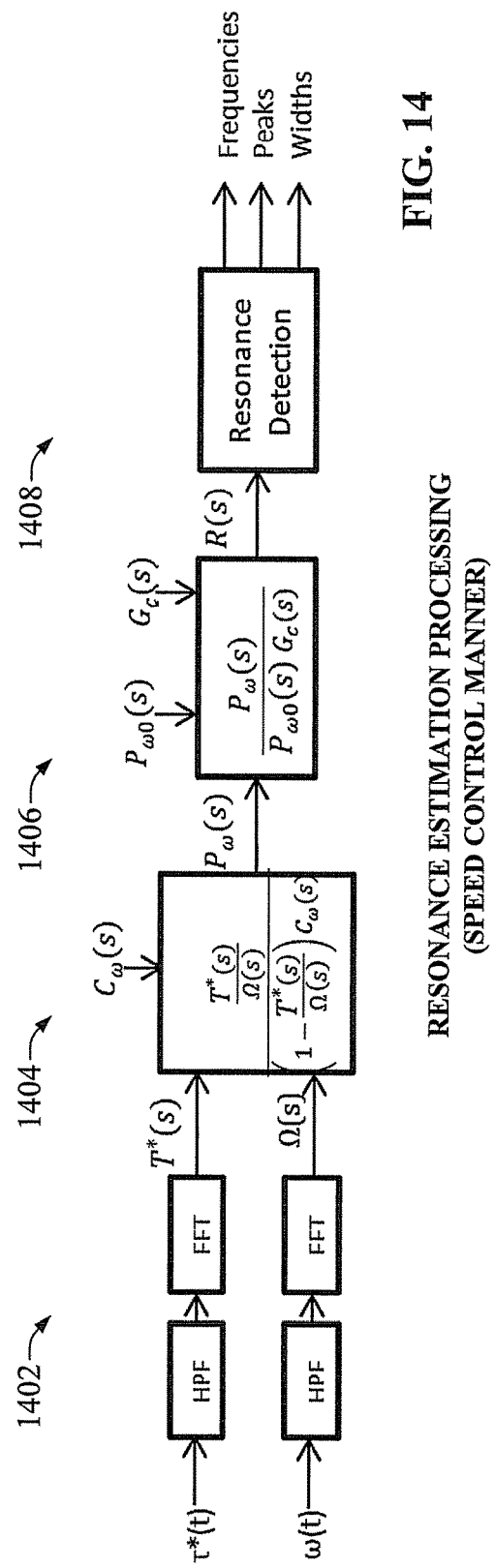
FIG. 14 is a block diagram illustrating processing performed on a torque reference and motor speed by a resonance determination component in a speed control scenario.

FIG. 14 is a block diagram illustrating processing performed on the torque reference $\tau^*(t)$ and motor speed $\omega(t)$ by the resonance determination component 312 in the speed control scenario. As in the torque control scenario, the torque reference $\tau^*(t)$ and measured motor speed $\omega(t)$ are high-pass filtered and fast Fourier transformed at 1402 to yield the frequency components $T^*(s)$ and $\Omega(s)$, respectively. For the speed control scenario, the speed plant transfer function is obtained at 1404 according to:

$$P_\omega(s) = \frac{\frac{T^*(s)}{\Omega(s)}}{\left(1 - \frac{T^*(s)}{\Omega(s)}\right)C_\omega(s)} \quad (17)$$

where $C_\omega(s)$ is the speed controller transfer function. The open-loop transfer function is obtained from the closed-loop transfer function, and the speed controller transfer function $C_\omega(s)$ is removed to obtain the speed plant transfer function.

Once the speed plant transfer function $P_\omega(s)$ is obtained at 1404, the resonance estimation component 312 removes the speed plant slow dynamics transfer function $P_{\omega 0}(s)$ and the torque (current q-axis) closed-loop transfer function $G_c(s)$ from the speed plant transfer function $P_\omega(s)$ at 1406, in a manner similar to processing step 906 described above. Finally, at 1408, the smoothing functions are applied to the resulting resonance data and the searching algorithm is used to identify the resonance information for the motion system, in a manner similar to step 908 above. Similar to the torque control scenario, the steps of injecting noise n(t) into torque reference and measuring the resulting motor speed feedback to determine the speed plant transfer function, and removing the slow dynamics of the motion and the fast torque control dynamics from the measured frequency response data to obtain the resonance information, can be repeated by system 302 multiple times and the results averaged in order to obtain average resonance information, which is then processed at step 1408 to identify the frequencies, peaks, and widths of the resonance(s).

Figure 15:
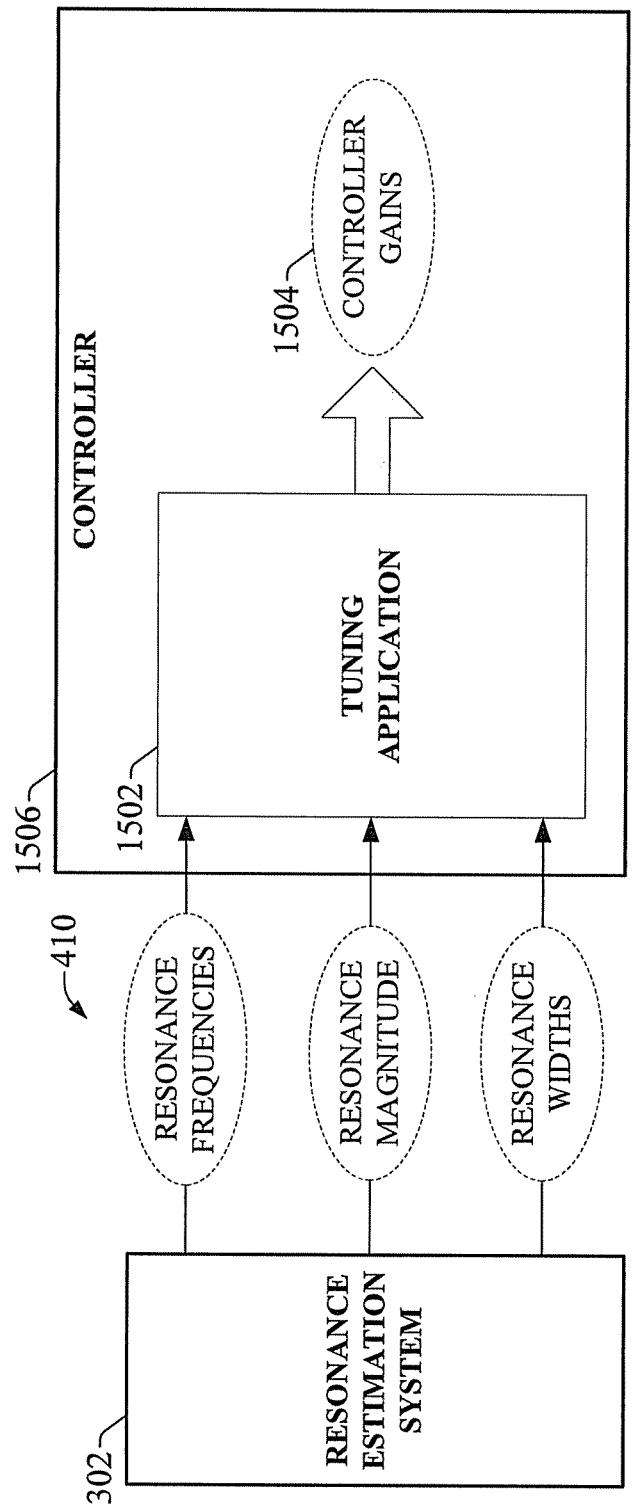
FIG. 15 is a diagram illustrating a system in which a resonance estimation system provides calculated resonance data to motion a controller.

In various embodiments, resonance estimation system 302 can output the calculated resonance frequency, peak, and/or width information in accordance with the requirements of a particular application in which the system operates. For example, FIG. 15 is a diagram illustrating a system in which resonance estimation system 302 provides the calculated resonance data 410 to motion controller 1506, which in this example scenario may include bandwidth optimization features that use the resonance data to facilitate tuning one or more controller gain coefficients. In particular, a tuning application 1502 that is an integrated component of controller 1506 may be configured to modify the controller's bandwidth or adjust one or more controller gains 1504 based on the resonance frequency information, the resonance magnitude information, or the resonance width information obtained by the resonance estimation system 302. Although FIG. 15 depicts resonance estimation system 302 as a separate system from controller 1506 that exchanges signaling and resonance data with the controller 1506 via any suitable communication means (e.g., wired or wireless network, hardwired data links, etc.), the estimation system 302 may be an integrated sub-system of the controller 1506 itself in some embodiments.

In another example application, rather than provide the calculated resonance data directly to a motion controller, the resonance estimation system 302 may render the resonance information on a display device via interface component 314. In such applications, a control system designer can reference the resonance information to configure or select a suitable vibration suppression system for use in counteracting the effects of the detected resonance of the motion system. For example, based on the frequency, magnitude, and/or width of a resonance detected by the resonance estimation system 302, the designer may configure a notch filter that introduces an appropriate anti-resonance designed to counteract the mechanical system's resonance. In another example, the designer may use the resonance information as a guide for implementing mechanical changes to the motion system intended to attenuate the effects of the resonance.

The resonance estimation system described herein can estimate the resonance presence in a motion system without the need for a high-resolution feedback signal, and without requiring high-frequency sampling of the feedback signal. This is achieved in part by the technique of solving for resonance information by removing the slow motion dynamics and fast torque control dynamics from the frequency response data obtained for the motion system. This is also achieved by the technique of using the phase peak to locate the general range of frequencies at which the resonance will be located, and locating the gain peak corresponding to the resonance frequency based on the location of the phase peak. These aspects facilitate acquisition of accurate resonance frequency and amplitude for a motion system without the need for a high-resolution encoder or high frequency sampling.

In the examples illustrated in FIGS. 5 and 15, resonance estimation system 302 is depicted as a separate system from the motion controller. For such configurations, any of components 304, 306, 308, 310, 312, and 314 can exchange data with the controller or other elements of the motion system via any suitable communications means, including but not limited to wired or wireless networking, hardwired data links, or other such communication means. In other embodiments, one or more of components 304, 306, 308, 310, 312, and 314 can be integrated components of a motion controller (e.g., an industrial controller such as a programmable logic controller, a system-on-chip or other type of microcontroller, etc.). For example, one or more of components 304, 306, 308, 310, 312, and 314 can be functional components of the controller's operating system and/or control software executed by one or more processors residing on the controller. Components 304, 306, 308, 310, 312, and 314 can also be hardware components residing within the controller, such as a circuit board or integrated circuit, that exchanges data with other functional elements of the controller. In some embodiments, resonance estimation system 302 may also be an integrated sub-system of a motor drive (e.g., a variable frequency drive or other motor drive). Other suitable implementations are also within the scope of certain embodiments of this disclosure.

Resonance estimation system 302 can be used in connection with substantially any type of motion control application, including but not limited to conveyor control systems, industrial robots (e.g., machining or material handling robots), industrial tooling systems, washing machines, conveyors, centrifuges, pumps, motorized hand tools, material handling systems, automotive systems (e.g., traction or propulsion systems of electric vehicles or other automotive systems), HVAC system components (e.g., fans, pumps, etc.), or other such motion control applications.

Figure 16A:
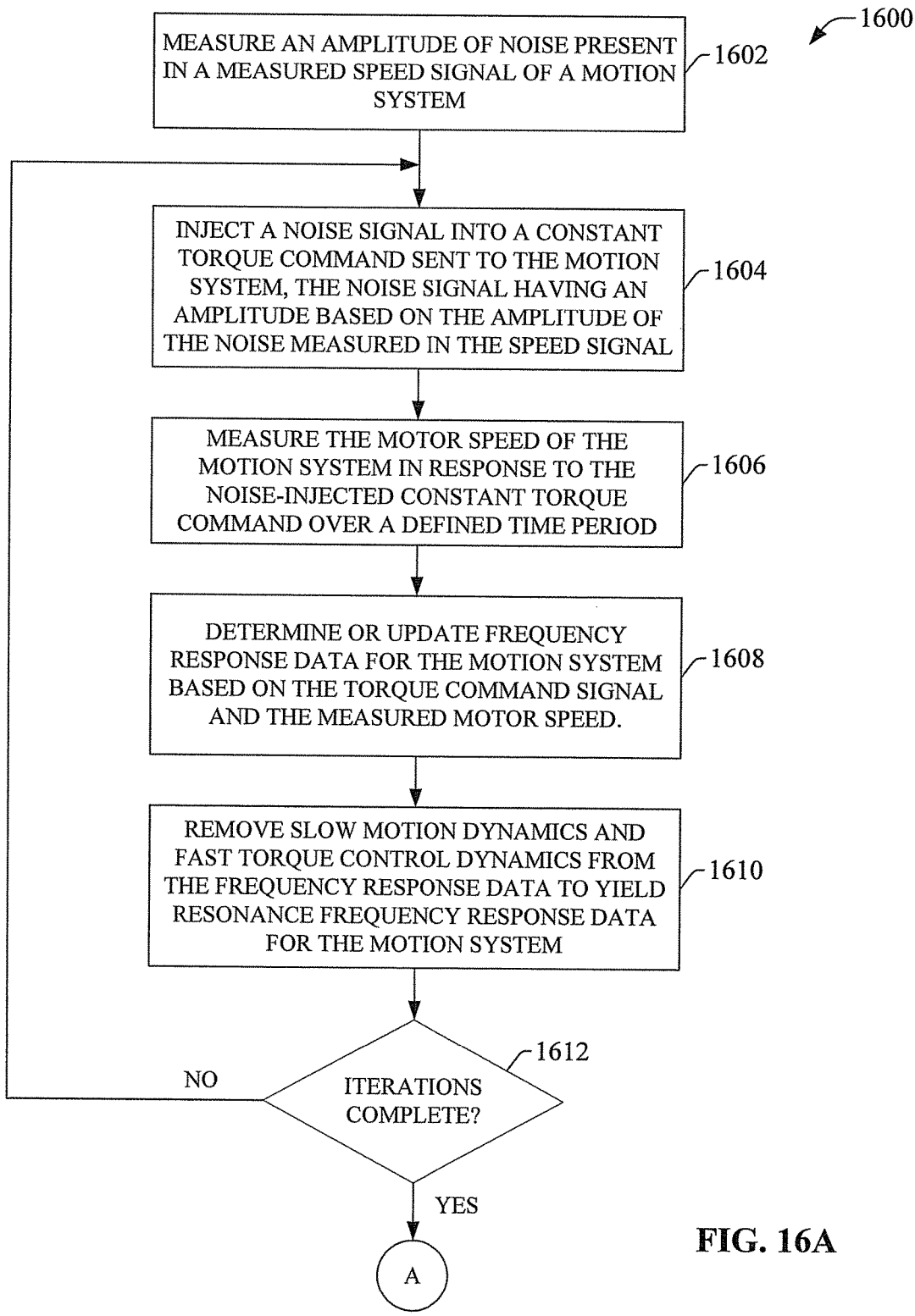
FIG. 16A and 16B are flowcharts of an example methodology for estimating resonance information for a motion system.
Figure 16B:
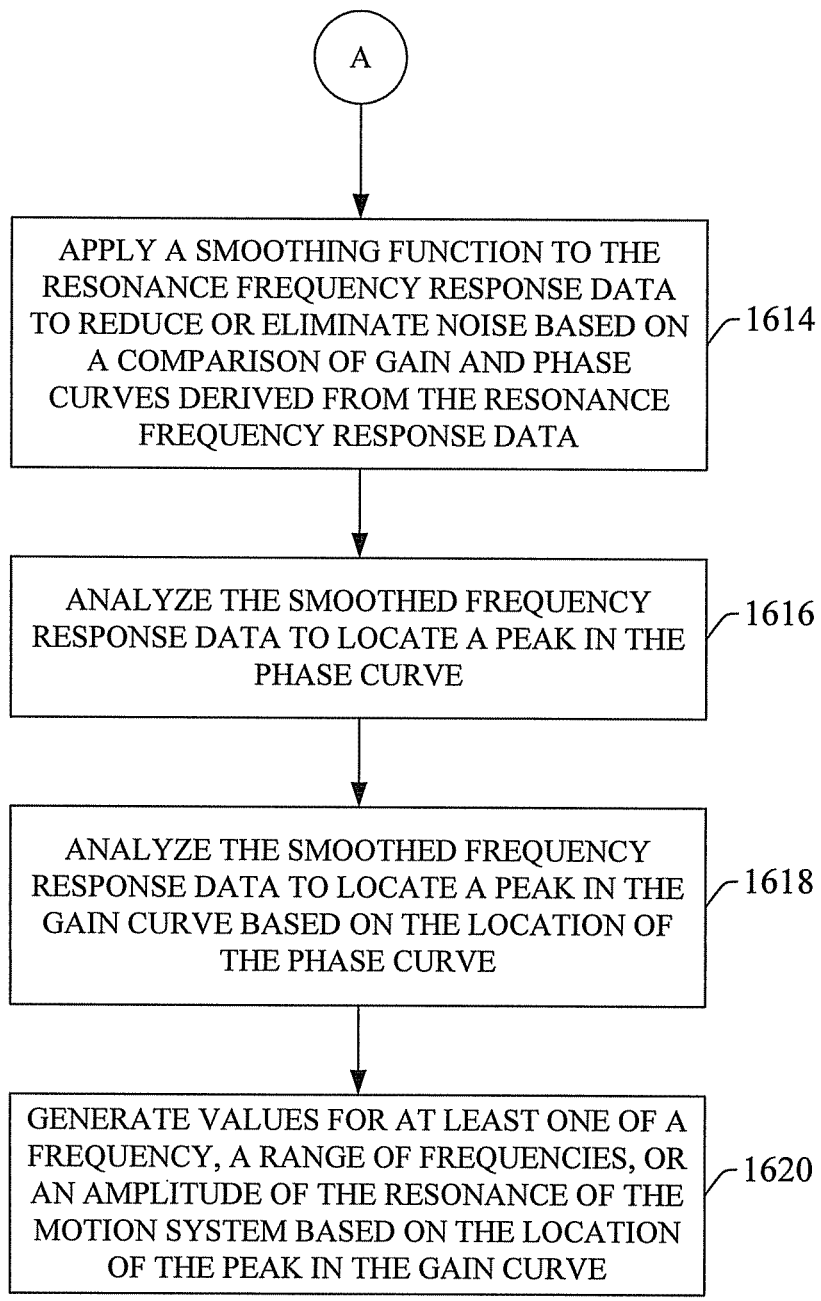

FIGS. 16A-16B illustrate a methodology in accordance with certain disclosed aspects. While, for purposes of simplicity of explanation, the methodology is shown and described as a series of acts, it is to be understood and appreciated that the disclosed aspects are not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with certain disclosed aspects. Additionally, it is to be further appreciated that the methodologies disclosed hereinafter and throughout this disclosure are capable of being stored on an article of manufacture to facilitate transporting and transferring such methodologies to computers.

FIG. 16A illustrates a first part of an example methodology 1600 for estimating resonance information for a motion system. Initially, at 1602, an amplitude of noise present in a speed signal representing a speed of the motion system is measured. For example, a resonance estimation system can generate a constant torque reference signal and measure the resulting speed of the motion system. When the speed signal has reached a steady state, the resonance estimation system can determine a level of noise present in the signal. The measured amplitude of the noise will be used as a baseline value for the next step.

At 1604, a noise signal is injected into a constant torque command sent to the motion system, where an amplitude of the noise signal is set based on the baseline noise value measured at step 1602. For example, the noise signal may be set to have an amplitude that is a multiple of the noise level measured at step 1602.

At 1606, the speed of the motor of the motion system in response to the noise-injected torque command generated at step 1604 is measured for a defined time period. The time period for which the noise-injected torque command is sent to the system at step 1604 and the corresponding motor speed is measured at step 1606 can be set to any suitable duration that allows a sufficient amount of data to be collected for calculation of the speed plant transfer function for the motion system.

At 1608, frequency response data for the motion system is determined (or updated) based on the noise-injected torque command signal generated at step 1604 and the corresponding measured motor speed data collected at step 1606. The frequency response data is characterized by the speed plant transfer function for the motion system. At 1610, in order to obtain resonance data from the frequency response data obtained at 1608, the slow motion dynamics and fast torque control dynamics are removed from the frequency response data. The information that remains after removal of the slow and fast dynamics represents the resonance frequency response data for the motion system.

At 1612, a determination is made as to whether a specified number of iterations of steps 1604-1610 have been performed. In some embodiments, the number of iterations to be carried out may be a preset value. Alternatively, the methodology may continue performing iterations of steps 1604-1610 until the resonance frequency response data 1610 satisfies a condition indicative of a substantially optimized result. For example, if the resonance frequency response data obtained at step 1610 for a most recent iteration is determined to be sufficiently similar to the data obtained from the previous iteration, the iteration cycle may be deemed complete.

If the specified number of iterations have not been completed (NO at step 1612), the methodology returns to step 1604, and steps 1604-1610 are repeated. The frequency response data obtained at step 1610 is updated based on results of this next iteration. Alternatively, if the specified number of iterations have been completed (YES at step 1612), the methodology proceeds to step 1614 of FIG. 16B, where a smoothing function is applied to the resonance frequency response data obtained via iterations of steps 1604-1610. The smoothing function is configured to reduce or eliminate noise from the resonance frequency response data, and is based on a comparison of the gain and phase curves derived from the resonance frequency response data. The smoothing function is based on an assumption that neither of the gain or phase curves should include a single frequency point spike with a large amplitude (e.g., a spike at a single frequency having an amplitude in excess of a defined threshold).

At 1616, the smoothed frequency response data obtained is analyzed to locate a peak in the phase curve derived from the frequency response data. For example, a searching algorithm can search for a peak in excess of a defined threshold amplitude, starting the search at the lowest frequencies and proceeding upward through higher frequencies until a peak in the phase curve satisfying a defined condition is located.

At 1618, the smoothed frequency response data is analyzed further to locate a peak in the gain curve based on the location of the phase peak discovered at step 1616. For example, a searching algorithm that carries out this analysis can be based on an assumption that a peak in the gain curve is expected to be located at a frequency that is higher, but near, the frequency corresponding to the peak in the phase curve found at step 1616. Accordingly, the searching algorithm may begin the search of the gain curve at the frequency of the discovered phase peak, and proceed through higher frequencies within the vicinity of the frequency of the phase peak unit a peak in the gain curve that satisfies a defined condition is located. The frequency (or range of frequencies) at which the peak in the gain curve is located corresponds to the frequency or frequency range of the resonance of the motion system.

At 1620, values for at least one of a frequency, a range of frequencies, or an amplitude of the motion system's resonance are generated based on the location of the peak in the gain curve, which itself is located based on the location of the peak in the phase curve. These obtain resonance values can be rendered via a display device so that a system designer can better configure the motion control system to compensate for the resonances present in the motion system. Alternatively, one or more of the resonance values can be provided to a motion controller or other system that sets a value of one or more controller gains or other motion control parameters based on the resonance data.

Exemplary Networked and Distributed Environments

One of ordinary skill in the art can appreciate that the various embodiments described herein can be implemented in connection with any computer or other client or server device, which can be deployed as part of a computer network or in a distributed computing environment, and can be connected to any kind of data store where media may be found. In this regard, the various embodiments of the resonance estimation system described herein can be implemented in any computer system or environment having any number of memory or storage units (e.g., memory 318 of FIG. 3), and any number of applications and processes occurring across any number of storage units. This includes, but is not limited to, an environment with server computers and client computers deployed in a network environment or a distributed computing environment, having remote or local storage. For example, with reference to FIG. 3, the torque command generator 304, velocity monitoring component 306, noise injection component 308, noise measurement component 310, resonance determination component 312, and interface component 314 can be stored on a single memory 318 associated with a single device, or can be distributed among multiple memories associated with respective multiple devices. Similarly, torque command generator 304, velocity monitoring component 306, noise injection component 308, noise measurement component 310, resonance determination component 312, and interface component 314 can be executed by a single processor 316, or by multiple distributed processors associated with multiple devices.

Distributed computing provides sharing of computer resources and services by communicative exchange among computing devices and systems. These resources and services include the exchange of information, cache storage and disk storage for objects. These resources and services can also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in the various embodiments of this disclosure.

Figure 17:
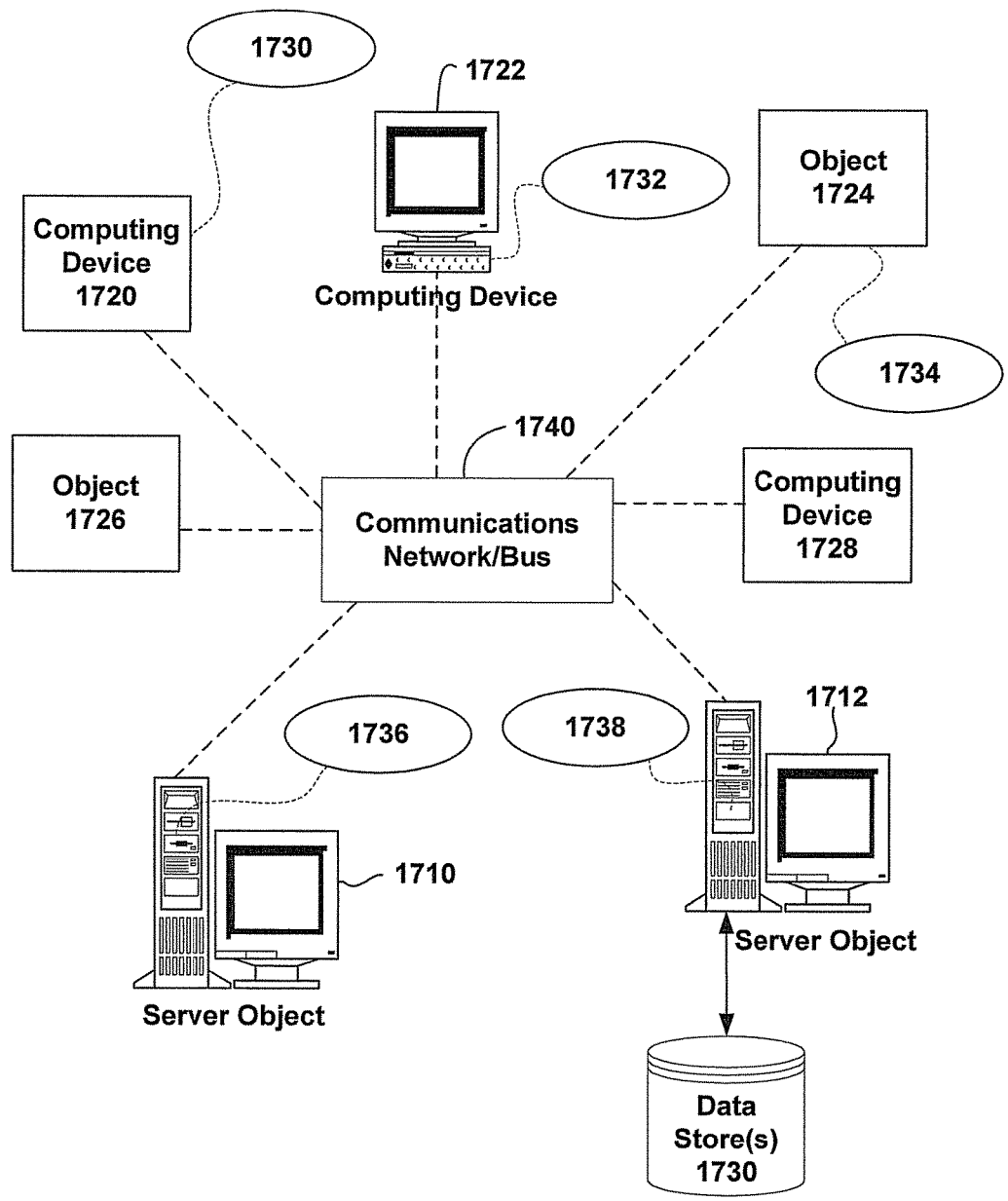
FIG. 17 is a block diagram representing an exemplary networked or distributed computing environment for implementing one or more embodiments described herein.

FIG. 17 provides a schematic diagram of an exemplary networked or distributed computing environment. The distributed computing environment includes computing objects 1710, 1712, etc. and computing objects or devices 1720, 1722, 1724, 1726, 1728, etc., which may include programs, methods, data stores, programmable logic, etc., as represented by applications 1730, 1732, 1734, 1736, 1738. It can be appreciated that computing objects 1710, 1712, etc. and computing objects or devices 1720, 1722, 1724, 1726, 1728, etc. may comprise different devices, such as personal digital assistants (PDAs), audio/video devices, mobile phones, MP3 players, personal computers, laptops, tablets, etc., where embodiments of the inertia estimator described herein may reside on or interact with such devices.

Each computing object 1710, 1712, etc. and computing objects or devices 1720, 1722, 1724, 1726, 1728, etc. can communicate with one or more other computing objects 1710, 1712, etc. and computing objects or devices 1720, 1722, 1724, 1726, 1728, etc. by way of the communications network 1740, either directly or indirectly. Even though illustrated as a single element in FIG. 17, communications network 1740 may comprise other computing objects and computing devices that provide services to the system of FIG. 17, and/or may represent multiple interconnected networks, which are not shown. Each computing object 1710, 1712, etc. or computing objects or devices 1720, 1722, 1724, 1726, 1728, etc. can also contain an application, such as applications 1730, 1732, 1734, 1736, 1738 (e.g., resonance estimation system 302 or components thereof), that might make use of an API, or other object, software, firmware and/or hardware, suitable for communication with or implementation of various embodiments of this disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any suitable network infrastructure can be used for exemplary communications made incident to the systems as described in various embodiments herein.

Thus, a host of network topologies and network infrastructures, such as client/server, peer-to-peer, or hybrid architectures, can be utilized. The "client" is a member of a class or group that uses the services of another class or group. A client can be a computer process, e.g., roughly a set of instructions or tasks, that requests a service provided by another program or process. A client process may utilize the requested service without having to "know" all working details about the other program or the service itself.

In a client/server architecture, particularly a networked system, a client can be a computer that accesses shared network resources provided by another computer, e.g., a server. In the illustration of FIG. 17, as a non-limiting example, computing objects or devices 1720, 1722, 1724, 1726, 1728, etc. can be thought of as clients and computing objects 1710, 1712, etc. can be thought of as servers where computing objects 1710, 1712, etc. provide data services, such as receiving data from client computing objects or devices 1720, 1722, 1724, 1726, 1728, etc., storing of data, processing of data, transmitting data to client computing objects or devices 1720, 1722, 1724, 1726, 1728, etc., although any computer can be considered a client, a server, or both, depending on the circumstances. Any of these computing devices may be processing data, or requesting transaction services or tasks that may implicate the techniques for systems as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the techniques described herein can be provided standalone, or distributed across multiple computing devices or objects.

In a network environment in which the communications network/bus 1740 is the Internet, for example, the computing objects 1710, 1712, etc. can be Web servers, file servers, media servers, etc. with which the client computing objects or devices 1720, 1722, 1724, 1726, 1728, etc. communicate via any of a number of known protocols, such as the hypertext transfer protocol (HTTP). Computing objects 1710, 1712, etc. may also serve as client computing objects or devices 1720, 1722, 1724, 1726, 1728, etc., as may be characteristic of a distributed computing environment.

Exemplary Computing Device

Figure 18:
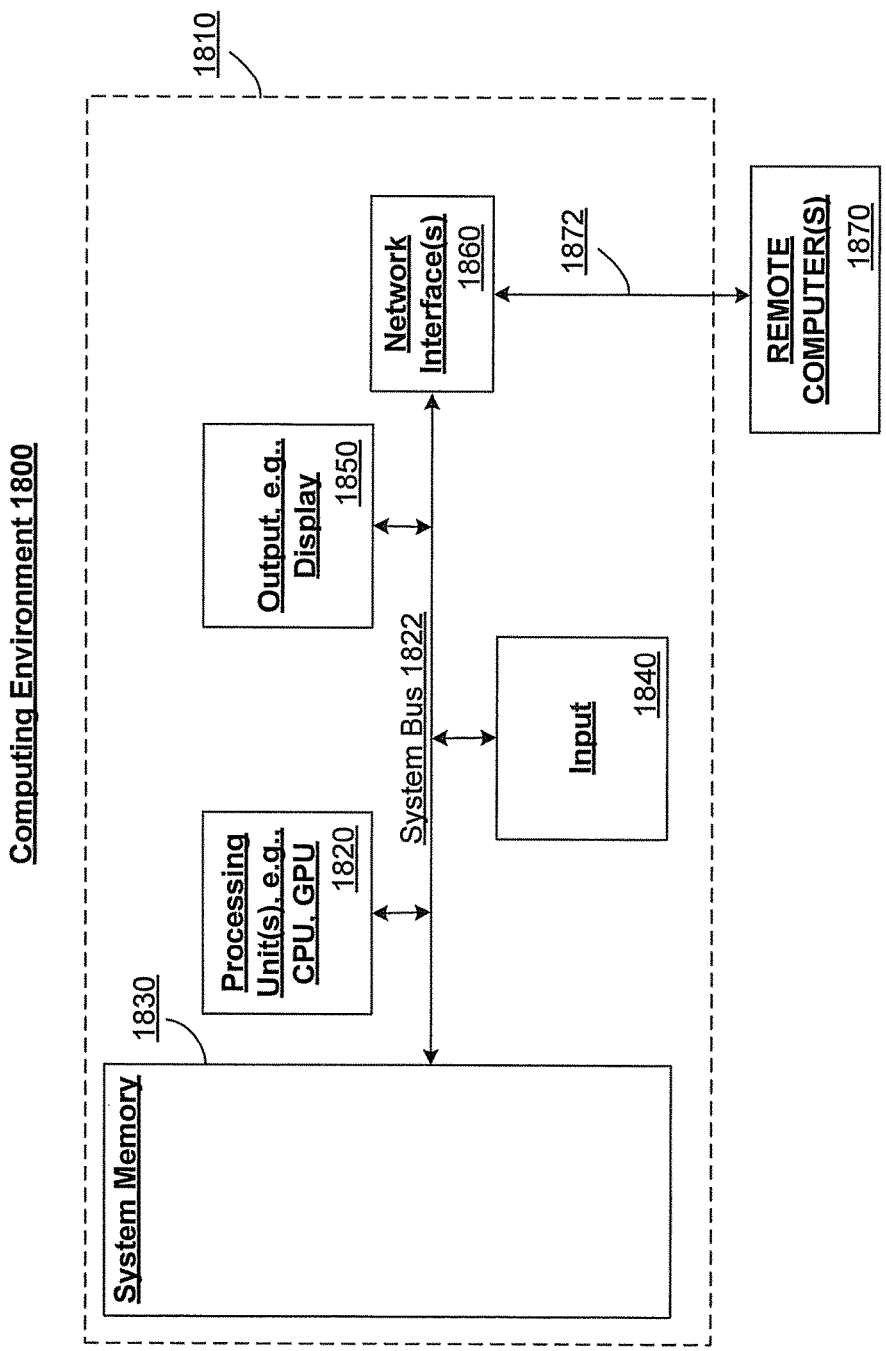
FIG. 18 is a block diagram representing an exemplary computing system or operating environment for implementing one or more embodiments described herein.

As mentioned, advantageously, the techniques described herein can be applied to any suitable device. It is to be understood, therefore, that handheld, portable and other computing devices and computing objects of all kinds are contemplated for use in connection with the various embodiments. Accordingly, the below computer described below in FIG. 18 is but one example of a computing device. Additionally, a suitable server can include one or more aspects of the below computer, such as a media server or other media management server components.

Although not required, embodiments can partly be implemented via an operating system, for use by a developer of services for a device or object, and/or included within application software that operates to perform one or more functional aspects of the various embodiments described herein. Software may be described in the general context of computer executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is to be considered limiting.

FIG. 18 thus illustrates an example of a suitable computing system environment 1800 in which one or aspects of the embodiments described herein can be implemented, although as made clear above, the computing system environment 1800 is only one example of a suitable computing environment and is not intended to suggest any limitation as to scope of use or functionality. Neither is the computing system environment 1800 be interpreted as having any dependency or requirement relating to any one or combination of components illustrated in the exemplary computing system environment 1800.

With reference to FIG. 18, an exemplary computing device for implementing one or more embodiments in the form of a computer 1810 is depicted. Components of computer 1810 may include, but are not limited to, a processing unit 1820, a system memory 1830, and a system bus 1822 that couples various system components including the system memory to the processing unit 1820. Processing unit 1820 may, for example, perform functions associated with processor(s) 316 of resonance estimation system 302, while system memory 1830 may perform functions associated with memory 318.

Computer 1810 typically includes a variety of computer readable media and can be any available media that can be accessed by computer 1810. The system memory 1830 may include computer storage media in the form of volatile and/or nonvolatile memory such as read only memory (ROM) and/or random access memory (RAM). By way of example, and not limitation, system memory 1830 may also include an operating system, application programs, other program modules, and program data.

A user can enter commands and information into the computer 1810 through input devices 1840, non-limiting examples of which can include a keyboard, keypad, a pointing device, a mouse, stylus, touchpad, touchscreen, trackball, motion detector, camera, microphone, joystick, game pad, scanner, or any other device that allows the user to interact with computer 1810. A monitor or other type of display device is also connected to the system bus 1822 via an interface, such as output interface 1850. In addition to a monitor, computers can also include other peripheral output devices such as speakers and a printer, which may be connected through output interface 1850. In one or more embodiments, input devices 1840 can provide user input to interface component 314, while output interface 1850 can receive information relating to operations of the resonance estimation system 302 from interface component 314.

The computer 1810 may operate in a networked or distributed environment using logical connections to one or more other remote computers, such as remote computer 1870. The remote computer 1870 may be a personal computer, a server, a router, a network PC, a peer device or other common network node, or any other remote media consumption or transmission device, and may include any or all of the elements described above relative to the computer 1810. The logical connections depicted in FIG. 18 include a network 1872, such local area network (LAN) or a wide area network (WAN), but may also include other networks/buses e.g., cellular networks.

As mentioned above, while exemplary embodiments have been described in connection with various computing devices and network architectures, the underlying concepts may be applied to any network system and any computing device or system in which it is desirable to publish or consume media in a flexible way.

Also, there are multiple ways to implement the same or similar functionality, e.g., an appropriate API, tool kit, driver code, operating system, control, standalone or downloadable software object, etc. which enables applications and services to take advantage of the techniques described herein. Thus, embodiments herein are contemplated from the standpoint of an API (or other software object), as well as from a software or hardware object that implements one or more aspects described herein. Thus, various embodiments described herein can have aspects that are wholly in hardware, partly in hardware and partly in software, as well as in software.

The word "exemplary" is used herein to mean serving as an example, instance, or illustration. For the avoidance of doubt, the aspects disclosed herein are not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has,"

"contains," and other similar words are used in either the detailed description or the claims, for the avoidance of doubt, such terms are intended to be inclusive in a manner similar to the term "comprising" as an open transition word without precluding any additional or other elements.

Computing devices typically include a variety of media, which can include computer-readable storage media (e.g., memory 318) and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function (e.g., coding and/or decoding); software stored on a computer readable medium; or a combination thereof.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is to be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In order to provide for or aid in the numerous inferences described herein (e.g. inferring audio segments), components described herein can examine the entirety or a subset of the data to which it is granted access and can provide for reasoning about or infer states of the system, environment, etc. from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

In view of the exemplary systems described above, methodologies that may be implemented in accordance with the described subject matter will be better appreciated with reference to the flowcharts of the various figures (e.g., FIGS. 16A and 16B). While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

In addition to the various embodiments described herein, it is to be understood that other similar embodiments can be used or modifications and additions can be made to the described embodiment(s) for performing the same or equivalent function of the corresponding embodiment(s) without deviating there from. Still further, multiple processing chips or multiple devices can share the performance of one or more functions described herein, and similarly, storage can be effected across a plurality of devices. Accordingly, the invention is not to be limited to any single embodiment, but rather can be construed in breadth, spirit and scope in accordance with the appended claims.

What is claimed is:

1. A system, comprising:
   a memory;
   a processor configured to execute components stored on the memory, the components comprising:
   a torque command generator configured to generate torque command data;
   a noise injection component configured to inject a noise signal into the torque command data to yield noise-injected torque command data;
   a velocity monitoring component configured to obtain speed data representing a speed of a motion system over time in response to a torque command signal generated based on the noise-injected torque command data; and
   a resonance determination component configured to generate, based on the speed data and the noise-injected torque command data, resonance frequency response data comprising resonance gain frequency response data and resonance phase frequency response data, and to determine a resonance frequency of the motion system based on a determined frequency of a phase peak in the resonance phase frequency response data.

2. The system of claim 1, wherein the resonance determination component is further configured to perform a high-pass filtering and a fast Fourier transform on the noise-injected torque command data and the speed data to yield transformed torque data and transformed speed data, respectively, and to generate the resonance frequency response data based on the transformed torque data and the transformed speed data.

3. The system of claim 1, wherein the resonance determination component is configured to generate frequency response data for the motion system based on the noise-injected torque command data and the speed data, and to remove slow motion dynamics data and fast torque control dynamics data for the motion system from the frequency response data to yield the resonance frequency response data.

4. The system of claim 3, wherein the resonance determination component is further configured to identify noise in the resonance frequency response data based on a comparison of the resonance gain frequency response data and the resonance phase frequency response data, and to remove the noise from the resonance frequency response data prior to determining the resonance frequency.

5. The system of claim 3, wherein the resonance determination component is further configured to estimate an inertia and a viscous friction coefficient of the motion system based on a measured velocity of the motion system in response to a stable torque command signal, and to determine the slow motion dynamics data based on the inertia and the viscous friction coefficient.

6. The system of claim 1, wherein the resonance determination component is configured to identify the phase peak in the resonance phase frequency response data based on an analysis of the resonance phase frequency response data, to identify a gain peak in the resonance gain frequency response data based on the frequency of the phase peak, and to determine the resonance frequency based on a frequency of the gain peak.

7. The system of claim 6, wherein the resonance determination component is further configured to identify a resonance amplitude based on a magnitude of the gain peak.

8. The system of claim 1, further comprising a noise measurement component configured to measure a baseline noise level in a speed signal measured from the motion system in response to another torque command signal that does not include the noise signal, wherein the noise injection component is configured to set a magnitude of the noise signal based on the baseline noise level.

9. A method, comprising:
   generating, by a system comprising at least one processor, torque command data representing a constant torque command;
   adding, by the system, noise data to the torque command data to yield noise-injected torque command data;
   generating, by the system, a torque command signal based on the noise-injected torque command data;
   measuring, by the system, speed data representing a speed of a motion system over time in response to the torque command signal;
   generating, by the system based on the speed data and the noise-injected torque command data, resonance frequency response data comprising resonance gain frequency response data and resonance phase frequency response data;
   identifying, by the system, a phase peak in the resonance phase frequency response data; and
   determining, by the system, a resonance frequency of the motion system based on a determined frequency of the phase peak.

10. The method of claim 9, wherein the generating the resonance frequency response data comprises:
    performing a first high-pass filtering and a first fast Fourier transform on the noise-injected torque command data to yield transformed torque data;
    performing a second high-pass filtering and a second fast Fourier transform on the speed data to yield transformed speed data; and
    generating the resonance gain frequency response data and the resonance phase frequency response data based on the transformed torque data and the transformed speed data.

11. The method of claim 9, wherein the generating the resonance frequency response data comprises:
    generating frequency response data for the motion system based on the noise-injected torque command data and the speed data; and
    removing slow motion dynamics data for the motion system and fast torque control dynamics data for the motion system from the frequency response data to yield the resonance frequency response data.

12. The method of claim 11, further comprising:
    identifying, by the system, noise in the resonance frequency response data based on a comparison of the resonance gain frequency response data and the resonance phase frequency response data; and
    removing, by the system, the noise from the resonance frequency response data prior to the identifying of the phase peak.

13. The method of claim 11, wherein the removing the slow motion dynamic data comprises:
    estimating an inertia and a viscous friction coefficient of the motion system based on a measured velocity of the motion system in response to a stable torque command signal; and
    determining the slow motion dynamic data based on the inertia and the viscous friction coefficient.

14. The method of claim 11, wherein the generating the resonance frequency response data further comprises:

performing multiple iterations of the generating of the frequency response data and the removing of the slow motion dynamics data and the fast torque control dynamics data from the frequency response data to yield multiple sets of resonance frequency response data; and generating the resonance frequency response data based on an averaging of the multiple sets of the resonance frequency response data.

15. The method of claim 9, wherein the determining the resonance frequency of the motion system comprises:

identifying a gain peak in the resonance gain frequency response data based on the determined frequency of the phase peak; and determining the resonance frequency based on a frequency of the gain peak.

16. The method of claim 15, further comprising determining, by the system, a resonance amplitude of the motion system based on a magnitude of the gain peak.

17. The method of claim 9, further comprising:

measuring, by the system, a baseline noise level in a speed signal measured from the motion system in response to another torque command signal that does not include the noise signal; and setting, by the system, a magnitude of the noise signal based on the baseline noise level.

\* \* \* \* \*